United States Patent
Cahoon et al.

(10) Patent No.: US 7,195,887 B2
(45) Date of Patent: Mar. 27, 2007

(54) RICE 1-DEOXY-D-XYLULOSE 5-PHOSPHATE SYNTHASE AND DNA ENCODING THEREOF

(75) Inventors: Rebecca E. Cahoon, Webster Grove, MO (US); Yong Tao, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/498,487

(22) Filed: Aug. 3, 2006

(65) Prior Publication Data

US 2006/0272056 A1 Nov. 30, 2006

Related U.S. Application Data

(62) Division of application No. 10/427,590, filed on Apr. 30, 2003, now Pat. No. 7,132,250, which is a division of application No. 09/857,556, filed as application No. PCT/US99/28587 on Dec. 2, 1999, now Pat. No. 6,558,915.

(60) Provisional application No. 60/110,779, filed on Dec. 3, 1998.

(51) Int. Cl.
*C12Q 1/48* (2006.01)
*C12N 9/10* (2006.01)
*C12N 15/29* (2006.01)
*A01H 5/00* (2006.01)
*C07H 21/04* (2006.01)

(52) U.S. Cl. .................... 435/15; 435/193; 435/252.3; 435/254.2; 435/320.1; 435/348; 435/410; 435/468; 536/23.2; 800/282; 800/298; 800/320.2

(58) Field of Classification Search .................... None
See application file for complete search history.

(56) References Cited

OTHER PUBLICATIONS

B. Markus Lange et al., PNAS, vol. 95:2100-2104, 1998, A family of transketolases that directs isoprenoid biosynthesis via a mevalonate-independent pathway.
EMBL Sequence Library Database Accession No. AF019383, May 6, 1998, B.M. Lange et al., A family of transketolases that directs isoprenoid biosynthesis via a mevalonate-independent pathway.
EMBL Sequence Library Database Accession No. AJ011840, Oct. 7, 1998, M. Clastre et al., A *Catharanthus roseus* cDNA encoding 1-deoxyxylulose 5-phosphate.
EMBL Sequence Library Database Accession No. O82676, Nov. 1, 1998, M. Clastre et al., A *Catharanthus roseus* cDNA encoding 1-deoxyxylulose 5-phosphate synthase.
EMBL Sequence Library Database Accession No. Q38854, Jul. 15, 1998, M. A. Mandel et al., CLA1, a novel gene required for chloroplast development, is high conserved in evolution.
Alejandra Mandel et al., Plant J., vol. 9(5):649-658, 1996, CLA1, a novel gene required for chloroplast development, is high conserved in evolution.
EMBL Sequence Library Database Accession No. Y15782, Sep. 7, 1998, F. Bouvier et al., Dedicated roles of plastid transketolases during the early onset isoprenoid biogenesis in pepper fruits.
Florence Bouvier et al., Plant Physiol., vol. 117:1423-1431, 1998, Dedicated roles of plastid transketolases during the early onset isoprenoid biogenesis in pepper fruits.
Luisa Maria Lois et al., PNAS, vol. 95:2105-2110, 1998, Cloning and characterization of a gene from *Escherichia coli* encoding a transketolase-like enzyme that catalyzes the synthesis of D-1-deoxyxylulose 5-phosphate, a common precursor for isoprenoid, thiamin, and pyridoxol biosynthesis.
Georg A. Sprenger et al., PNAS, vol. 94:12857-12862, 1997, Identification of a thiamin-dependent synthase in *Escerichia coli* required for the formation of the 1-deoxy-D-xylulose 5-phosphate precursor to isoprenoids, thiamin, and pyridoxol.
National Center for Biotechnology Information General Identifier No. 3559816, Sep. 7, 1998, Bouvier, F. et al., Dedicated roles of plastid transketolases during the early onset isoprenoid biogenesis in pepper fruits.
National Center for Biotechnology Information General Identifier No. 5803266, Jun. 2, 2000, T. Sasaki et al., Oryza sativa nipponbare(GA3) genomic DNA, chromosome 6, PAC clone:P0535G04.
National Center for Biotechnology Information General Identifier No. 3913239, Aug. 20, 2001, Campos, N. et al., Nucleotide sequence of a rice encoding a transketolase-like protein homologous to the *Arabidopsis* CLA1 gene product.
National Center for Biotechnology Information General Identifier No. 3724087, Oct. 7, 1998, M. Clastre, A *Catharanthus roseus* cDNA encoding 1-deoxyxylulose 5-phosphate synthase.
National Center for Biotechnology Information General Identifier No. 5059160, May 4, 2001, Lois L.M. et al., Carotenoid biosynthesis during tomato fruit development: regulatory role of 1-deoxy-D-xylulose 5-phosphate synthase.
L. M. Lois et al., Plant J., vol. 22(6):503-513, 2000, Carotenoid biosynthesis during tomato fruit development: regulatory role of 1-deoxy-D-xylulose 5-phosphate synthase.
Arthur L. Fredeen, Effects of phosphorus nutrition on photosynthesis in Glycine max (L.) Merr., Planta, 1990, vol. 181:399-405.

*Primary Examiner*—Elizabeth Slobodyansky

(57) ABSTRACT

This invention relates to an isolated nucleic acid fragment encoding an isopentenyl diphosphate biosynthetic enzyme. The invention also relates to the construction of a chimeric gene encoding all or a portion of the isopentenyl diphosphate biosynthetic enzyme, in sense or antisense orientation, wherein expression of the chimeric gene results in production of altered levels of the isopentenyl diphosphate biosynthetic enzyme in a transformed host cell.

13 Claims, 4 Drawing Sheets

FIGURE 1A

```
SEQ ID NO:33   MALCAYAFPGILNRTVAVASDASKPTPL----FSEWIHGTDLQFQFHQKLTQ-VKKRSRT
SEQ ID NO:10   MSLSAFSFPLHLRQTTPPSDPKTSSTPLPSSHSHW--GADLLTQSQRKL-NQVKRRPHG
SEQ ID NO:12   MDLSALS---------SYRTLGKLLPLPSHSQW--GLHFLAHAHR-L-HQMKKRPCG
SEQ ID NO:26   MALTTFSI---------SRGGFVGALPQEGHFA-PAAAELSLHKLQSRPHKARRRSSS
SEQ ID NO:34   ------------------------------------------------------------
                1                                                           60

SEQ ID NO:33   -VQASLS---ESGEYYTQRPPTPIVDTINYPIHMKNLSLKELKQLADELRSDTIFNVSKT
SEQ ID NO:10   -VCASLS---EMGEYYSQKPPTPLLDTINYPIHMKNLATKKLKQLADELRSDVIFHVSRT
SEQ ID NO:12   -VYASLS---ESGEYYSHRPPTPLLDTVNYPIHMKNLSAKELKQLADELRSDVIFSVSRT
SEQ ID NO:26   SISASLSTEREAAEYHSQRPPTPLLDTVNYPIHMKNLSLKELQQLADELRSDVIFHVSKT
SEQ ID NO:34   ------------------NYPIHMKNLSLKELQQLADELRSDVIFHVSKT
                          *          *  *  **********  * ********** **   **
                61                                                         120

SEQ ID NO:33   GGHLGSSLGVVELTVALHYVFNAPQDRILWDVGHQSYPHKILTGRREKMSTLRQTNGLAG
SEQ ID NO:10   GGHLGSSLGVVELTIALHYVFNAPKDKILWDVGHQSYPHKILTGRRDKMHTMRQTDGLAG
SEQ ID NO:12   GGHLGSSLGVVELTVALHYVFNAPQDKILWDVGHQSYPHKILTGRRDQMHTMRQTNGLSG
SEQ ID NO:26   GGHLGSSLGVVELTVALHYVFNTPQDKILWDVGHQSYPHKILTGRRDKMPTMRQTNGLSG
SEQ ID NO:34   GGHLGSSLGVVELTVALHYVFNTPQDKILWDVGHQSYPHKILTGRRDKMPTMRQTNGLSG
                ************** * ***** * *************** *   *  ** ***
                121                                                        180
```

FIGURE 1B

```
                  *******   * ************      ***  *****************
SEQ ID NO:33      FTKRSESEYDCFGTGHSSTTISAGLGMAVGRDLKGRNNNVIAVIGDGAMTAGQAYEAMNN
SEQ ID NO:10      FTKRSESDYDCFGTGHSSTTISAGLGMAVGRDLKGDKNNVVAVIGDGAMTAGQAYEAMNN
SEQ ID NO:12      FTKRSESEFDCFGTGHSSTTISAGLGMAVGRDLKGRKNNVVAVIGDGAMTAGQAYEAMNN
SEQ ID NO:26      FTKRSESEYDSFGTGHSSTTISAALGMAVGRDLKGGKNNVVAVIGDGAMTAGQAYEAMNN
SEQ ID NO:34      FTKRSESEYDSFGTGHSSTTISAALGMAVGRDLKGGKNNVVAVIGDGAMTAGQAYEAMNN
                  181                                                        240

**************  ********                ****   *************
SEQ ID NO:33      AGYLDSDMIVILNDNRQVSLPTATLDGPVPPVPPVGALSSALSRLQSNRPLRELREVAKGVTK
SEQ ID NO:10      AGYLDSDMIVILNDNKQVSLPTANLDGPIPPVGALSSALSSALSKLQSNRPLRELREVAKGVTK
SEQ ID NO:12      AGYLDSDMIVILNDNKQVSLPTATLDGPIPPVGALSSALSRLQSNRPLRELREVAKGVTK
SEQ ID NO:26      AGYLDSDMIVILNDNKQVSLPTATLDGPAPPVGALSSALSKLQSSRPLRELREVAKGVTK
SEQ ID NO:34      AGYLDSDMIVILNDNKQVSLPTATLDGPAPPVGALSSALSKLQSSRPLRELREVAKGVTK
                  241                                                        300

***    ********************     ***************  ** *** ****
SEQ ID NO:33      QIGGPMHELAAKVDEYARGMISGSGSTLFEELGLYYIGPVDGHNIDDLISILKEVRSTKT
SEQ ID NO:10      QIGGPMHELAAKVDEYARGMISGSGSTLFEELGLYYIGPVDGHNIDDLVSILNEVKSTKT
SEQ ID NO:12      RIGGPMHELAAKVDEYARGMISGSGSLFEELGLYYIGPVDGHNIDDLVAILNEVKSTKT
SEQ ID NO:26      QIGGSVHELAAKVDEYARGMISGSGSTLFEELGLYYIGPVDGHNIDDLITILREVKSTKT
SEQ ID NO:34      QIGGSVHELAAKVDEYARGMISGSGSTLFEELGLYYIGPVDGHNIDDLITILREVKSTKT
                  301                                                        360
```

FIGURE 1C

```
              ******  ** *****  *******  **********  ****  ********   *  *  ***  **********
SEQ ID NO:33  TGPVLIHVVTEKGRGYPYAERAADKYHGVAKFDPATGKQFKGSAKTQSYTTYFAEALIAE
SEQ ID NO:10  TGPVLLHVVTEKGHGYPYAERAADKYHGVTKFDPATGKQFKSNAATQSYTTYFAEALIAE
SEQ ID NO:12  TGPVLIHVITEKGRGYPYAEKAADKYHGVTKFDPPTGKQFKSKATTQSYTTYFAEALIAE
SEQ ID NO:26  TGPVLIHVVTEKGRGYPYAERAADKYHGVAKFDPATGKQFKSPAKTLSYTNYFAEALIAE
SEQ ID NO:34  TGPVLIHVVTEKGRGYPYAERAADKYHGVAKFDPATGKQFKSPAKTLSYTNYFAEALIAE
              361                                                       420

** *   *  **************  *  ****  *************************
SEQ ID NO:33  AEADKDIVAIHAAMGGGTGMNLFLRRFPTRCFDVGIAEQHAVTFAAGLACEGLKPFCAIY
SEQ ID NO:10  AEADKDIVGIHAAMGGGTGMNLFLRRFPTRCFDVGIAEQHAVTFAAGLACEGLKPFCAIY
SEQ ID NO:12  AEADKDVVAIHAAMGGGTGMNLFHRRFPTRCFDVGIAEQHAVTFAAGLACEGLKPFCAIY
SEQ ID NO:26  AEQDNRVVAIHAAMGGGTGLNYFLRRFPNRCFDVGIAEQHAVTFAAGLACEGLKPFCAIY
SEQ ID NO:34  AEQDNRVVAIHAAMGGGTGLNYFLRRFPNRCFDVGIAEQHAVTFAAGLACEGLKPFCAIY
              421                                                       480

***  **  *************************  ****  ******************
SEQ ID NO:33  SSFMQRAYDQVVHDVDLQKLPVRFAMDRAGLVGADGPTHCGAFDVTFMACLPNMVVMAPS
SEQ ID NO:10  SSFMQRAYDQVVHDVDLQKLPVRFAMDRAGLVGADGPTHCGAFDVTFMACLPNMVVMAPS
SEQ ID NO:12  SSFMQRAYDQVVHDVDLQKLPVRFAMDRAGLVGADGPTHCGSFDVTFMACLPNMVVMAPS
SEQ ID NO:26  SSFLQRGYDQVVHDVDLQKLPVRFAMDRAGLVGADGPTHCGAFDVTYMACLPNMVVMAPS
SEQ ID NO:34  SSFLQRGYDQVVHDVDLQKLPVRFAMDRAGLVGADGPTHCGAFDVTYMACLPNMVVMAPS
              481                                                       540
```

FIGURE 1D

```
                        ***  *  * ********  ************ **  ** *** ****  *  * *** ***** **  ********
SEQ ID NO:33           DEAELFHIVATAAAIDDRPSCFRYPRGNGIGVELPAGNKGIPLEVGKGRILVEGERVALL
SEQ ID NO:10           DEAELFHMVATAAAIDDRPSCFRYPRGNGIGVELPLGNKGIPLEIGKGRILIEGERVALL
SEQ ID NO:12           DEADLFHMVATAAAINDRPSCFRYPRGNGIGVQLPTGNKGTPLEIGKGRILIEGERVALL
SEQ ID NO:26           DEAELCHMVATAAAIDDRPSCFRYPRGNGIGVPLPPNYKGVPLEVGKGRVLLEGERVALL
SEQ ID NO:34           DEAELCHMVATAAAIDDRPSCFRYPRGNGIGVPLPPNYKGVPLEVGKGRVLLEGERVALL
                                                                                   600
                       541

********  *******  *  *  **  *********** *** *  ***  ****** *** ***** **  *******
SEQ ID NO:33           GYGSAVQNCLAAASVLESRGLQVTVADARFCKPLDRALIRSLAKSHEVLVTVEKGSIGGF
SEQ ID NO:10           GYGSAVQSCLAAASLLEHHGLRATVADARFCKPLDRSLIRSLIRSLAQSHEVLITVEEGSIGGF
SEQ ID NO:12           GYGSAVQNCLAAASLVECHGLRLTVADARFCKPLDRSLIRSLAKSHEVLITVEEGSIGGF
SEQ ID NO:26           GYGSAVQYCLAAASLVERHGLKVTVADARFCKPLDQTLIRRLASSHEVLLTVEEGSIGGF
SEQ ID NO:34           GYGSAVQYCLAAASLVERHGLKVTVADARFCKPLDQTLIRRLASSHEVLLTVEEGSIGGF
                                                                                   660
                       601

****  *********** ****
SEQ ID NO:33           GSHVVQFMALDGLLDGKLKWRPIVLPDRYIDHGSPADQLAEAGLTPSHIAATVFNILGQTREALEVMT----
SEQ ID NO:10           GSHVVQFMALDGLLDGKLKWRPIVLPDCYIDHGSPVDQLSAAGLTPSHIAATVFNLLGQTREALEVMT----
SEQ ID NO:12           GSHVAQFMALDGLLDGKLKWRPIVLPDRYIDHGSPADQLSLAGLTPSHIAATVFNVLGQTREALEVMS----
SEQ ID NO:26           GSHVAQFMALDGLLDGKLKWRPLVLPDRYIDHGSPADQLAEAGLTPSHIAATVFNVLGQAREALAIMTVPNA
SEQ ID NO:34           GSHVAQFMALDGLLDGKLKWRP-------------------------------------------------
                                                                                   732
                       661
```

SEQUENCE LISTING

```
<160> NUMBER OF SEQ ID NOS: 34

<210> SEQ ID NO 1
<211> LENGTH: 738
<212> TYPE: DNA
<213> ORGANISM: Zea mays
<220> FEATURE:
<221> NAME/KEY: unsure
<222> LOCATION: (634)
<223> OTHER INFORMATION: n = A, C, G or T
<220> FEATURE:
<221> NAME/KEY: unsure
<222> LOCATION: (636)
<223> OTHER INFORMATION: n = A, C, G or T
<220> FEATURE:
<221> NAME/KEY: unsure
<222> LOCATION: (661)
<223> OTHER INFORMATION: n = A, C, G or T
```

```
<220> FEATURE:
<221> NAME/KEY: unsure
<222> LOCATION: (672)
<223> OTHER INFORMATION: n = A, C, G or T
<220> FEATURE:
<221> NAME/KEY: unsure
<222> LOCATION: (695)
<223> OTHER INFORMATION: n = A, C, G or T
<220> FEATURE:
<221> NAME/KEY: unsure
<222> LOCATION: (713)
<223> OTHER INFORMATION: n = A, C, G or T
<220> FEATURE:
<221> NAME/KEY: unsure
<222> LOCATION: (717)
<223> OTHER INFORMATION: n = A, C, G or T

<400> SEQUENCE: 1
gagaatgaca agcgcattgt ggtagttcat ggcggcatgg gaatcgatcg atcactccgc    60
ttattccagt ccaggttccc agacagattt tttgacttgg gcatcgctga gcaacatgct   120
gttaccttt ctgctggttt ggcctgcgga ggtctaaagc ctttctgcat aattccatcc   180
acatttcttc agcgagcata tgatcagata attgaagatg tggacatgca aaagatacca   240
gttcgttttg ctatcacaaa tgctggtctg gtaggatctg agggtccaac taattcagga   300
ccatttgata ttacattcat gtcatgcttg ccaaacatga ttgtcatgtc accatctaat   360
gaggatgaac ttattgacat ggtggcaaca gctgcaatga ttgaggacag acctatttgc   420
ttccgctatc ctaggggtgc cattgttggg actagtggaa gtgtaacata tgggaatcca   480
tttgagattg gtaaaggaga gattcttgtc gagggaaaag agatagcttt tcttggctat   540
ggcgaggtgg tccagagatg cttgattgct cgatcccttt tatccaactt gggcattcag   600
gcgacagttg caaatgcgag gttttgcaag ccgntntgac agcggaccta atccagaacg   660
ntgttgccag cncatgagtt tttcttgacc acagnggaaa gaaaggaacg gtntggnagg   720
gctttgggag caacaggt                                                 738

<210> SEQ ID NO 2
<211> LENGTH: 211
<212> TYPE: PRT
<213> ORGANISM: Zea mays

<400> SEQUENCE: 2

Glu Asn Asp Lys Arg Ile Val Val His Gly Gly Met Gly Ile Asp
  1               5                  10                  15

Arg Ser Leu Arg Leu Phe Gln Ser Arg Phe Pro Asp Arg Phe Asp
             20                  25                  30

Leu Gly Ile Ala Glu Gln His Ala Val Thr Phe Ser Ala Gly Leu Ala
         35                  40                  45

Cys Gly Gly Leu Lys Pro Phe Cys Ile Ile Pro Ser Thr Phe Leu Gln
     50                  55                  60

Arg Ala Tyr Asp Gln Ile Glu Asp Val Asp Met Gln Lys Ile Pro
 65                  70                  75                  80

Val Arg Phe Ala Ile Thr Asn Ala Gly Leu Val Gly Ser Glu Gly Pro
                 85                  90                  95

Thr Asn Ser Gly Pro Phe Asp Ile Thr Phe Met Ser Cys Leu Pro Asn
            100                 105                 110

Met Ile Val Met Ser Pro Ser Asn Glu Asp Glu Leu Ile Asp Met Val
        115                 120                 125

Ala Thr Ala Ala Met Ile Glu Asp Arg Pro Ile Cys Phe Arg Tyr Pro
    130                 135                 140
```

```
Arg Gly Ala Ile Val Gly Thr Ser Gly Ser Val Thr Tyr Gly Asn Pro
145                 150                 155                 160

Phe Glu Ile Gly Lys Gly Glu Ile Leu Val Glu Gly Lys Glu Ile Ala
                165                 170                 175

Phe Leu Gly Tyr Gly Glu Val Val Gln Arg Cys Leu Ile Ala Arg Ser
            180                 185                 190

Leu Leu Ser Asn Leu Gly Ile Gln Ala Thr Val Ala Asn Ala Arg Phe
        195                 200                 205

Cys Lys Pro
    210

<210> SEQ ID NO 3
<211> LENGTH: 415
<212> TYPE: DNA
<213> ORGANISM: Zea mays
<220> FEATURE:
<221> NAME/KEY: unsure
<222> LOCATION: (11)..(13)
<223> OTHER INFORMATION: n = A, C, G or T
<220> FEATURE:
<221> NAME/KEY: unsure
<222> LOCATION: (386)
<223> OTHER INFORMATION: n = A, C, G or T
<220> FEATURE:
<221> NAME/KEY: unsure
<222> LOCATION: (395)
<223> OTHER INFORMATION: n = A, C, G or T

<400> SEQUENCE: 3
agcagatgga nnnactcagt gcacgagctg gcggcgaagt ggacgagtac gcccgcggca      60
tgatcagcgg gcccggctcc tcgctcttcg aggagctcgg tctctactac atcggccccg    120
tcgacggcca caacatcgac gacctcatca ccatcctcaa cgacgtcaag agcaccaaga    180
ccaccggccc cgtcctcatc cacgtcgtca ccgagaaggg ccgcggctac ccctacgccg    240
agcgagccgc cgacaagtac cacggtgtcg ccaagtttga tccggcgacc gggaagcagt    300
tcaagtcccc cgccaagacg ctgtcctaca ccaactactt cgccgaggcg ctcatcgccg    360
aggcggagca ggacagcaag atcgtnggca tccangcggc catgggggcg gacgg         415

<210> SEQ ID NO 4
<211> LENGTH: 131
<212> TYPE: PRT
<213> ORGANISM: Zea mays
<220> FEATURE:
<221> NAME/KEY: UNSURE
<222> LOCATION: (127)
<223> OTHER INFORMATION: Xaa = ANY AMINO ACID

<400> SEQUENCE: 4

Ser Val His Glu Leu Ala Ala Glu Val Asp Glu Tyr Ala Arg Gly Met
1               5                   10                  15

Ile Ser Gly Pro Gly Ser Ser Leu Phe Glu Glu Leu Gly Leu Tyr Tyr
                20                  25                  30

Ile Gly Pro Val Asp Gly His Asn Ile Asp Asp Leu Ile Thr Ile Leu
            35                  40                  45

Asn Asp Val Lys Ser Thr Lys Thr Thr Gly Pro Val Leu Ile His Val
        50                  55                  60

Val Thr Glu Lys Gly Arg Gly Tyr Pro Tyr Ala Glu Arg Ala Ala Asp
65                  70                  75                  80

Lys Tyr His Gly Val Ala Lys Phe Asp Pro Ala Thr Gly Lys Gln Phe
                85                  90                  95
```

Lys Ser Pro Ala Lys Thr Leu Ser Tyr Thr Asn Tyr Phe Ala Glu Ala
            100                 105                 110

Leu Ile Ala Glu Ala Glu Gln Asp Ser Lys Ile Val Gly Ile Xaa Ala
        115                 120                 125

Ala Met Gly
    130

<210> SEQ ID NO 5
<211> LENGTH: 717
<212> TYPE: DNA
<213> ORGANISM: Oryza sativa
<220> FEATURE:
<221> NAME/KEY: unsure
<222> LOCATION: (581)
<223> OTHER INFORMATION: n = A, C, G or T
<220> FEATURE:
<221> NAME/KEY: unsure
<222> LOCATION: (663)
<223> OTHER INFORMATION: n = A, C, G or T
<220> FEATURE:
<221> NAME/KEY: unsure
<222> LOCATION: (676)
<223> OTHER INFORMATION: n = A, C, G or T
<220> FEATURE:
<221> NAME/KEY: unsure
<222> LOCATION: (687)
<223> OTHER INFORMATION: n = A, C, G or T
<220> FEATURE:
<221> NAME/KEY: unsure
<222> LOCATION: (709)
<223> OTHER INFORMATION: n = A, C, G or T

<400> SEQUENCE: 5
cttacatgtc ctttctccac ctcggtggtc atcagctaga cagctatcgc gcgccgtccc      60
accaccatct tgctccacta ccgcggacca ccgcgcgcga gcagagcatc tcctcactct     120
ctagcttgct ccagtttcgc gtagctgcgt gacagttcaa ttgaactctc tggattcgtt     180
ggttacttcg tctgagctgc tgcagcgttg aggaggagga ggagcaatgg cgctcacgac     240
gttctccatt tcgagaggag gcttcgtcgg cgcgctgccg caggagggc atttcgctcc      300 ggcggcggcg gagctcagtc tccacaagct ccagagcagg ccacacaagg ctaggcggag     360
gtcgtccgtc gagcatctcg gcgtcgctgt ccacgggaga gggaggcggc ggatacaatc     420
gcaagcggca ccgacgccgc tgctggacac gtcaaactac cccatccaca tgaaagaact     480
gtccctcaaa ggactccagc aactcgccga cgagctcgct ccgactcatc ctcactctcc     540
aaagaccggg ggacatctcg ggtccaacct cggcgtcgtc naactcaccg tcgcgctcca     600
ctaactgttc aacaccctca ggacaagatc tctgggactc ggcacaatcg tacctcacaa     660
aantctgacg gcggngcga caagatncga caagcgtaga caacggttnt cggaatc        717

<210> SEQ ID NO 6
<211> LENGTH: 125
<212> TYPE: PRT
<213> ORGANISM: Oryza sativa
<220> FEATURE:
<221> NAME/KEY: UNSURE
<222> LOCATION: (119)
<223> OTHER INFORMATION: Xaa = ANY AMINO ACID

<400> SEQUENCE: 6

Met Ala Leu Thr Thr Phe Ser Ile Ser Arg Gly Gly Phe Val Gly Ala
 1               5                  10                  15

Leu Pro Gln Glu Gly His Phe Ala Pro Ala Ala Ala Glu Leu Ser Leu
            20                  25                  30

```
His Lys Leu Gln Ser Arg Pro His Lys Ala Arg Arg Ser Ser Val
            35                  40                  45

Glu His Leu Gly Val Ala Val His Gly Arg Gly Arg Arg Ile Gln
    50                  55                  60

Ser Gln Ala Ala Pro Thr Pro Leu Leu Asp Thr Ser Asn Tyr Pro Ile
65                  70                  75                  80

His Met Lys Glu Leu Ser Leu Lys Gly Leu Gln Gln Leu Ala Asp Glu
                85                  90                  95

Leu Ala Pro Thr His Pro His Ser Pro Lys Thr Gly Gly His Leu Gly
                100                 105                 110

Ser Asn Leu Gly Val Val Xaa Leu Thr Val Ala Leu His
                115                 120                 125

<210> SEQ ID NO 7
<211> LENGTH: 494
<212> TYPE: DNA
<213> ORGANISM: Oryza sativa
<220> FEATURE:
<221> NAME/KEY: unsure
<222> LOCATION: (19)
<223> OTHER INFORMATION: n = A, C, G or T
<220> FEATURE:
<221> NAME/KEY: unsure
<222> LOCATION: (29)
<223> OTHER INFORMATION: n = A, C, G or T
<220> FEATURE:
<221> NAME/KEY: unsure
<222> LOCATION: (44)
<223> OTHER INFORMATION: n = A, C, G or T
<220> FEATURE:
<221> NAME/KEY: unsure
<222> LOCATION: (71)
<223> OTHER INFORMATION: n = A, C, G or T
<220> FEATURE:
<221> NAME/KEY: unsure
<222> LOCATION: (77)
<223> OTHER INFORMATION: n = A, C, G or T
<220> FEATURE:
<221> NAME/KEY: unsure
<222> LOCATION: (95)
<223> OTHER INFORMATION: n = A, C, G or T
<220> FEATURE:
<221> NAME/KEY: unsure
<222> LOCATION: (110)
<223> OTHER INFORMATION: n = A, C, G or T
<220> FEATURE:
<221> NAME/KEY: unsure
<222> LOCATION: (122)
<223> OTHER INFORMATION: n = A, C, G or T
<220> FEATURE:
<221> NAME/KEY: unsure
<222> LOCATION: (146)
<223> OTHER INFORMATION: n = A, C, G or T
<220> FEATURE:
<221> NAME/KEY: unsure
<222> LOCATION: (164)
<223> OTHER INFORMATION: n = A, C, G or T
<220> FEATURE:
<221> NAME/KEY: unsure
<222> LOCATION: (167)
<223> OTHER INFORMATION: n = A, C, G or T
<220> FEATURE:
<221> NAME/KEY: unsure
<222> LOCATION: (195)
<223> OTHER INFORMATION: n = A, C, G or T
<220> FEATURE:
<221> NAME/KEY: unsure
<222> LOCATION: (238)
<223> OTHER INFORMATION: n = A, C, G or T
<220> FEATURE:
<221> NAME/KEY: unsure
<222> LOCATION: (285)
```

```
<223> OTHER INFORMATION: n = A, C, G or T
<220> FEATURE:
<221> NAME/KEY: unsure
<222> LOCATION: (330)
<223> OTHER INFORMATION: n = A, C, G or T
<220> FEATURE:
<221> NAME/KEY: unsure
<222> LOCATION: (363)
<223> OTHER INFORMATION: n = A, C, G or T
<220> FEATURE:
<221> NAME/KEY: unsure
<222> LOCATION: (365)
<223> OTHER INFORMATION: n = A, C, G or T
<220> FEATURE:
<221> NAME/KEY: unsure
<222> LOCATION: (382)
<223> OTHER INFORMATION: n = A, C, G or T
<220> FEATURE:
<221> NAME/KEY: unsure
<222> LOCATION: (417)
<223> OTHER INFORMATION: n = A, C, G or T
<220> FEATURE:
<221> NAME/KEY: unsure
<222> LOCATION: (460)
<223> OTHER INFORMATION: n = A, C, G or T
<220> FEATURE:
<221> NAME/KEY: unsure
<222> LOCATION: (466)
<223> OTHER INFORMATION: n = A, C, G or T
<220> FEATURE:
<221> NAME/KEY: unsure
<222> LOCATION: (469)
<223> OTHER INFORMATION: n = A, C, G or T

<400> SEQUENCE: 7
acatacatat gcacacaana ttctcacang aagggctca ctcnttcata ctattaagca      60
aagaaagggg ntttcangtt tcacatcccg tttcnagagc gaatatgatn cctttggtgc    120
angacatgga tgcaataatc tctccncaag ccttgggatg gcantcncaa gggatctaag    180
tgggaggaaa aaccnaatag taacagttat aagtaactgg acaactatgg ctggtcangt    240
gtatgaggca atgggtcatg ccggtttcct tgattctaac atggnagtga ttttaaatga    300
caagccggga caccttgctt cctaaagcan atagccaatc aaagatgtct attaatgccc    360
tcncnaatgc tctgagcaaa gntcaatcca acaaaaggat ttataaagtt taaggangt    420 gcaaagggga ctttccaaat ggttttggta aaggaagcn atgaanttnc tgccaaaaat    480
tattaatatg cccc                                                    494

<210> SEQ ID NO 8
<211> LENGTH: 21
<212> TYPE: PRT
<213> ORGANISM: Oryza sativa
<220> FEATURE:
<221> NAME/KEY: UNSURE
<222> LOCATION: (15)
<223> OTHER INFORMATION: Xaa = ANY AMINO ACID

<400> SEQUENCE: 8

Val Tyr Glu Ala Met Gly His Ala Gly Phe Leu Asp Ser Asn Xaa Met
 1               5                  10                  15

Val Ile Leu Asn Asp
                20

<210> SEQ ID NO 9
<211> LENGTH: 2583
<212> TYPE: DNA
<213> ORGANISM: Glycine max

<400> SEQUENCE: 9
```

```
atgattacgc caagcgcgca attaaccctc actaaaggga acaaaagctg gagctccacc      60
gcggtggcgg ccgctctaga actagtggat ccccgggct gcaggaattc ggcacgaggt      120
gaagttcacc ttgttcctca caataattct ctcctacctc ttgtgttttg cttcagtcat     180
gtctctctct gcattctcat tccctctcca tctgagacaa acaacaccac cttctgatcc     240
taaaacatca tcaaccccctt tgcctttgtc ttctcactcc cattgggtg cagatctgct     300
cacacaatcc caacgcaaac tcaaccaggt gaaaagaagg ccacatgggg tatgtgcatc    360
actatcagaa atgggggagt attattctca gaaacctcct actccactgt ggacaccat     420
aaactatcca attcacatga gaatttggc taccaagaaa ctgaaacaac ttgcggatga     480
gctgcgttct gatgttattt ccatgtttc tagaactggg ggtcatttgg gatctagcct    540
tggtgttgta gaactcacta ttgcccttca ctatgttttc aatgctccta aggacaaaat   600
tttgtgggat gttggtcatc agtcttatcc tcataagata ctcactggta aagggataa    660
gatgcatacc atgaggcaga cagatggatt ggccgggttt acaaaacgat ctgagagtga   720
ttatgattgt tttggcactg gtcacagctc cacaacaata tcagcaggac tgggaatggc   780
tgttgggagg gatctgaagg gagacaagaa taatgtagtt gctgttatcg gtgatggtgc    840
tatgacggct ggtcaagctt atgaagccat gaacaacgct ggatatcttg attccgacat   900
gattgttatt ctaaatgaca acaagcaggt ctccctacca actgctaatc tcgatggtcc   960
cataccacct gtaggtgctt tgagtagtgc tctcagtaag ttacaatcaa acagacctct  1020
tagagaactc agagaggttg ctaagggagt cactaaacaa attggtggcc caatgcatga  1080
gttagctgca aaagttgatg aatatgcgcg tggcatgatc agcggttctg gatcaacact  1140
atttgaagag cttggacttt actacatagg tcctgttgat ggtcataata tagatgatct  1200
tgtgtccatt ctaaatgaag ttaaaagtac taaacaact ggtcctgtgc tgctccatgt   1260
tgtcactgaa aaaggccatg gatatccata tgcagaaaga gcagcagaca agtaccatgg  1320
agttactaag tttgatccag caactggaaa acaattcaaa tccaatgctg ccacccagtc  1380
atacacaaca tactttgcag aggctttaat tgctgaagcg gaagctgaca aagacattgt  1440
cggaatccat gctgcaatgg gaggtggaac tggcatgaat ctcttccttc gccgtttccc  1500
aacaagatgc tttgatgtgg ggatagcaga acagcatgct gttacatttg cggctggtct  1560
ggcttgtgaa ggccttaagc ctttttgtgc aatttactca tcatttatgc agagagctta  1620
tgaccaggtg gtgcatgatg tcgatttgca gaagctgcct gtaagattcg caatggaccg  1680
agccggatta gttggagcag atggtcccac acactgcggt gcatttgatg tcacttttat  1740
ggcatgcctc cctaacatgg tggtgatggc tccttctgat gaagcagagc ttttttcacat  1800
ggttgcaact gcagctgcca ttgatgatcg acccagttgt ttccgatacc cgaggggaaa  1860
tggtattggt gttgagctac cactagggaa taaaggcatt cctcttgaga ttgggaaggg  1920
taggatacta attgaaggag aaagagtggc cttgttgggc tatggatcag ctgttcagag  1980
ctgtctggct gctgcttcct tgttggaaca tcatggcttg cgcgcaacag tggcggatgc  2040
acgtttctgc aagccattgg accgttccct tattcgcagc cttgcccaat cgcacgaggt  2100
tttgatcact gtggaagaag ggtcaatagg aggattcgga tctcatgttg ttcagttcat  2160
ggcccttgat ggccttcttg atgggaaatt aaagtggagg ccaattgttc ttcctgattg   2220
ttacattgac catggatcac cggttgacca attgagtgca gctggtctta caccatctca  2280
catagcagca acagtttttca atctacttgg acaaacaaga gaggcactag aggtcatgac  2340
```

-continued

```
ataaaacaaa tgcaaagggg ttcaattttt gttccctgca atgtacaaag tagcgtgatt    2400
cacccagtgt aatacaaatg tgtttgttaa aaaataatag aaatggaaaa tgcagattga    2460
caaataatag tgccaacaaa tggttaaacg aataaaaaaa aaaaaaaaaa actcgagggg    2520
gggcccggta cccaattcgc cctatagtga gtcgtattac gcgcgctcac tggccgtcgt    2580
ttt                                                                  2583
```

<210> SEQ ID NO 10
<211> LENGTH: 721
<212> TYPE: PRT
<213> ORGANISM: Glycine max

<400> SEQUENCE: 10

```
Met Ser Leu Ser Ala Phe Ser Phe Pro Leu His Leu Arg Gln Thr Thr
 1               5                  10                  15

Pro Pro Ser Asp Pro Lys Thr Ser Ser Thr Pro Leu Pro Leu Ser Ser
            20                  25                  30

His Ser His Trp Gly Ala Asp Leu Leu Thr Gln Ser Gln Arg Lys Leu
        35                  40                  45

Asn Gln Val Lys Arg Arg Pro His Gly Val Cys Ala Ser Leu Ser Glu
    50                  55                  60

Met Gly Glu Tyr Tyr Ser Gln Lys Pro Pro Thr Pro Leu Leu Asp Thr
65                  70                  75                  80

Ile Asn Tyr Pro Ile His Met Lys Asn Leu Ala Thr Lys Lys Leu Lys
                85                  90                  95

Gln Leu Ala Asp Glu Leu Arg Ser Asp Val Ile Phe His Val Ser Arg
            100                 105                 110

Thr Gly Gly His Leu Gly Ser Ser Leu Gly Val Val Glu Leu Thr Ile
        115                 120                 125

Ala Leu His Tyr Val Phe Asn Ala Pro Lys Asp Lys Ile Leu Trp Asp
    130                 135                 140

Val Gly His Gln Ser Tyr Pro His Lys Ile Leu Thr Gly Arg Arg Asp
145                 150                 155                 160

Lys Met His Thr Met Arg Gln Thr Asp Gly Leu Ala Gly Phe Thr Lys
                165                 170                 175

Arg Ser Glu Ser Asp Tyr Asp Cys Phe Gly Thr Gly His Ser Ser Thr
            180                 185                 190

Thr Ile Ser Ala Gly Leu Gly Met Ala Val Gly Arg Asp Leu Lys Gly
        195                 200                 205

Asp Lys Asn Asn Val Val Ala Val Ile Gly Asp Gly Ala Met Thr Ala
    210                 215                 220

Gly Gln Ala Tyr Glu Ala Met Asn Asn Ala Gly Tyr Leu Asp Ser Asp
225                 230                 235                 240

Met Ile Val Ile Leu Asn Asp Asn Lys Gln Val Ser Leu Pro Thr Ala
                245                 250                 255

Asn Leu Asp Gly Pro Ile Pro Pro Val Gly Ala Leu Ser Ser Ala Leu
            260                 265                 270

Ser Lys Leu Gln Ser Asn Arg Pro Leu Arg Glu Leu Arg Glu Val Ala
        275                 280                 285

Lys Gly Val Thr Lys Gln Ile Gly Gly Pro Met His Glu Leu Ala Ala
    290                 295                 300

Lys Val Asp Glu Tyr Ala Arg Gly Met Ile Ser Gly Ser Gly Ser Thr
305                 310                 315                 320

Leu Phe Glu Glu Leu Gly Leu Tyr Tyr Ile Gly Pro Val Asp Gly His
```

```
                     325                 330                 335
Asn Ile Asp Asp Leu Val Ser Ile Leu Asn Glu Val Lys Ser Thr Lys
                340                 345                 350
Thr Thr Gly Pro Val Leu Leu His Val Thr Glu Lys Gly His Gly
            355                 360                 365
Tyr Pro Tyr Ala Glu Arg Ala Ala Asp Lys Tyr His Gly Val Thr Lys
        370                 375                 380
Phe Asp Pro Ala Thr Gly Lys Gln Phe Lys Ser Asn Ala Ala Thr Gln
385                 390                 395                 400
Ser Tyr Thr Thr Tyr Phe Ala Glu Ala Leu Ile Ala Glu Ala Glu Ala
                405                 410                 415
Asp Lys Asp Ile Val Gly Ile His Ala Ala Met Gly Gly Thr Gly
            420                 425                 430
Met Asn Leu Phe Leu Arg Arg Phe Pro Thr Arg Cys Phe Asp Val Gly
            435                 440                 445
Ile Ala Glu Gln His Ala Val Thr Phe Ala Ala Gly Leu Ala Cys Glu
            450                 455                 460
Gly Leu Lys Pro Phe Cys Ala Ile Tyr Ser Ser Phe Met Gln Arg Ala
465                 470                 475                 480
Tyr Asp Gln Val Val His Asp Val Asp Leu Gln Lys Leu Pro Val Arg
                485                 490                 495
Phe Ala Met Asp Arg Ala Gly Leu Val Gly Ala Asp Gly Pro Thr His
                500                 505                 510
Cys Gly Ala Phe Asp Val Thr Phe Met Ala Cys Leu Pro Asn Met Val
            515                 520                 525
Val Met Ala Pro Ser Asp Glu Ala Glu Leu Phe His Met Val Ala Thr
            530                 535                 540
Ala Ala Ala Ile Asp Asp Arg Pro Ser Cys Phe Arg Tyr Pro Arg Gly
545                 550                 555                 560
Asn Gly Ile Gly Val Glu Leu Pro Leu Gly Asn Lys Gly Ile Pro Leu
                565                 570                 575
Glu Ile Gly Lys Gly Arg Ile Leu Ile Glu Gly Glu Arg Val Ala Leu
            580                 585                 590
Leu Gly Tyr Gly Ser Ala Val Gln Ser Cys Leu Ala Ala Ala Ser Leu
        595                 600                 605
Leu Glu His His Gly Leu Arg Ala Thr Val Ala Asp Ala Arg Phe Cys
        610                 615                 620
Lys Pro Leu Asp Arg Ser Leu Ile Arg Ser Leu Ala Gln Ser His Glu
625                 630                 635                 640
Val Leu Ile Thr Val Glu Glu Gly Ser Ile Gly Gly Phe Gly Ser His
                645                 650                 655
Val Val Gln Phe Met Ala Leu Asp Gly Leu Leu Asp Gly Lys Leu Lys
            660                 665                 670
Trp Arg Pro Ile Val Leu Pro Asp Cys Tyr Ile Asp His Gly Ser Pro
        675                 680                 685
Val Asp Gln Leu Ser Ala Ala Gly Leu Thr Pro Ser His Ile Ala Ala
        690                 695                 700
Thr Val Phe Asn Leu Leu Gly Gln Thr Arg Glu Ala Leu Glu Val Met
705                 710                 715                 720
Thr

<210> SEQ ID NO 11
<211> LENGTH: 2517
```

<212> TYPE: DNA
<213> ORGANISM: Glycine max
<220> FEATURE:
<221> NAME/KEY: unsure
<222> LOCATION: (2438)
<223> OTHER INFORMATION: n = A, C, G or T
<220> FEATURE:
<221> NAME/KEY: unsure
<222> LOCATION: (2441)
<223> OTHER INFORMATION: n = A, C, G or T

<400> SEQUENCE: 11

```
ctatgaccat gattacgcca agcgcgcaat taaccctcac taaagggaac aaaagctgga    60
gctccaccgc ggtggcggcc gctctagaac tagtggatcc cccgggctgc aggaattcgg   120
caccagcatg gatctctccg ctctctcatc ataccgcact ctcgggaagt tacttcctct   180
tccctctcac tctcaatggg gtctccattt cctcgcccac gctcaccgcc tccaccagat   240
gaagaaaagg ccatgtgggg tatatgcatc cctctccgag agtggagagt attattccca   300
ccgaccgcca actcccctac tagacaccgt caactatcct attcatatga agaatctctc   360
tgccaaggag ctgaaacaac tcgcggatga actgcgttct gatgttattt tcagtgtttc   420
tagaactggg ggccatttgg gctcaagcct tggtgtggtg gaactcactg ttgcacttca   480
ctatgtcttc aatgcccctc aggacaagat actgtgggac gttggtcacc agtcttaccc   540
gcataagata ctcaccggta agggaccac gatgcatacc atgaggcaga caaatggctt   600
atctggcttc accaaacgtt ctgagagtga atttgattgt tttggcactg gtcacagctc   660
caccaccatt tcggcaggac ttggaatggc tgttgggagg gatctgaagg gaagaaagaa   720
taacgtggtt gctgttatag gcgatggtgc catgacagca gggcaagctt atgaagccat   780
gaacaatgct ggatatcttg attctgcat gattgttatt ctaaatgaca acaagcaggt   840
ttctttacca actgctactc ttgatggacc cataccacct gtaggagcct tgagtagcgc   900
tctcagtaga ttacaatcaa ataggcctct tagagaattg agagaggttg ccaagggagt   960
tactaaacga attggaggtc ctatgcatga attggctgca aaagttgacg agtatgctcg  1020
tggcatgatc agtggttctg gatcatcact ttttgaagag cttggactct actatattgg  1080
tcctgttgat ggtcataaca tagatgatct tgttgccatc ctcaacgaag ttaaaagtac  1140
taaaacaacc ggtcctgtat tgattcatgt tatcactgaa aaaggccgtg gatacccta  1200 tgcagaaaag gcagcagaca ataccatgg ggttaccaag tttgacccac caactggaaa  1260
gcaattcaaa tccaaggcta ccactcagtc ttacacaaca tactttgctg aggctttgat  1320
tgcagaagcc gaagctgaca agacgttgt tgcaatccat gctgctatgg gaggtggaac  1380
tggcatgaat ctcttccatc gccgtttccc aacaagatgc tttgatgtgg ggatagcaga  1440
acagcatgct gttacatttg ctgcaggtct ggcttgtgaa ggtcttaaac ctttctgtgc  1500
aatttactca tcattcatgc agagggctta tgaccaggtg gtgcatgatg tggatttgca  1560
gaagctgcct gtaagatttg caatggacag ggctggatta gttggagcag atggtcccac  1620
acattgtggt tcttttgatg tcacatttat ggcatgcctg cctaacatgg tggtgatggc  1680
tccttctgat gaagccgacc ttttccacat ggttgccacc gcagcagcca ttaatgatcg  1740
acctagttgt tttcgatacc aaggggaaa tggcattggt gttcagctac aactggaaa  1800 taaaggaact cctcttgaga ttgggaaagg taggatattg attgaagggg aaagagtggc  1860
tctcttgggc tatggatcag ctgttcagaa ctgtttggct gcagcttcct tagtggaatg  1920
tcatggcttg cgcttaacag ttgctgatgc acgtttctgc aaaccactgg atcggtccct  1980
```

-continued

```
gattcgcagc ctggcaaaat cacatgaggt tttaatcaca gttgaagaag gatcaattgg   2040
aggatttggt tctcatgttg ctcagttcat ggcccttgat ggccttctag atggcaaatt   2100
gaagtggcgg ccaatagttc ttccggatcg ttatatcgat catggatcac ctgctgacca   2160
attgtcttta gccggtctta caccatctca catagcagca acagtgttca atgtactagg   2220
acaaacaaga gaggcactag aggtcatgtc atagaaatat taaggggttc aattttttcac  2280 ttcacacgat gtacaaagta taacatgatt caccatgtgt aatatgaaaa agtaatgtaa   2340
tattgtgaaa ttttgaagtg tatgatgtag attgtcatat agtaaaacga ctagttataa   2400
aagagaaaaa tgttaaactt ttctttaaaa aaaaaaanaa naaaaaaaaa actcgagggg   2460
gggcccggta cccaattcgc cctatagtga gtcgtattac gcgcgctaca ctggcgt      2517
```

<210> SEQ ID NO 12
<211> LENGTH: 708
<212> TYPE: PRT
<213> ORGANISM: Glycine max

<400> SEQUENCE: 12

```
Met Asp Leu Ser Ala Leu Ser Ser Tyr Arg Thr Leu Gly Lys Leu Leu
  1               5                  10                  15

Pro Leu Pro Ser His Ser Gln Trp Gly Leu His Phe Leu Ala His Ala
                 20                  25                  30

His Arg Leu His Gln Met Lys Lys Arg Pro Cys Gly Val Tyr Ala Ser
             35                  40                  45

Leu Ser Glu Ser Gly Glu Tyr Tyr Ser His Arg Pro Thr Pro Leu
         50                  55                  60

Leu Asp Thr Val Asn Tyr Pro Ile His Met Lys Asn Leu Ser Ala Lys
 65                  70                  75                  80

Glu Leu Lys Gln Leu Ala Asp Glu Leu Arg Ser Asp Val Ile Phe Ser
                 85                  90                  95

Val Ser Arg Thr Gly Gly His Leu Gly Ser Ser Leu Gly Val Val Glu
            100                 105                 110

Leu Thr Val Ala Leu His Tyr Val Phe Asn Ala Pro Gln Asp Lys Ile
        115                 120                 125

Leu Trp Asp Val Gly His Gln Ser Tyr Pro His Lys Ile Leu Thr Gly
    130                 135                 140

Arg Arg Asp Gln Met His Thr Met Arg Gln Thr Asn Gly Leu Ser Gly
145                 150                 155                 160

Phe Thr Lys Arg Ser Glu Ser Glu Phe Asp Cys Phe Gly Thr Gly His
                165                 170                 175

Ser Ser Thr Thr Ile Ser Ala Gly Leu Gly Met Ala Val Gly Arg Asp
            180                 185                 190

Leu Lys Gly Arg Lys Asn Asn Val Val Ala Val Ile Gly Asp Gly Ala
        195                 200                 205

Met Thr Ala Gly Gln Ala Tyr Glu Ala Met Asn Asn Ala Gly Tyr Leu
    210                 215                 220

Asp Ser Asp Met Ile Val Ile Leu Asn Asp Asn Lys Gln Val Ser Leu
225                 230                 235                 240

Pro Thr Ala Thr Leu Asp Gly Pro Ile Pro Pro Val Gly Ala Leu Ser
                245                 250                 255

Ser Ala Leu Ser Arg Leu Gln Ser Asn Arg Pro Leu Arg Glu Leu Arg
            260                 265                 270

Glu Val Ala Lys Gly Val Thr Lys Arg Ile Gly Gly Pro Met His Glu
        275                 280                 285
```

```
Leu Ala Ala Lys Val Asp Glu Tyr Ala Arg Gly Met Ile Ser Gly Ser
    290                 295                 300
Gly Ser Ser Leu Phe Glu Leu Gly Leu Tyr Tyr Ile Gly Pro Val
305                 310                 315                 320
Asp Gly His Asn Ile Asp Asp Leu Val Ala Ile Leu Asn Glu Val Lys
                325                 330                 335
Ser Thr Lys Thr Thr Gly Pro Val Leu Ile His Val Ile Thr Glu Lys
            340                 345                 350
Gly Arg Gly Tyr Pro Tyr Ala Glu Lys Ala Ala Asp Lys Tyr His Gly
        355                 360                 365
Val Thr Lys Phe Asp Pro Pro Thr Gly Lys Gln Phe Lys Ser Lys Ala
    370                 375                 380
Thr Thr Gln Ser Tyr Thr Thr Tyr Phe Ala Glu Ala Leu Ile Ala Glu
385                 390                 395                 400
Ala Glu Ala Asp Lys Asp Val Val Ala Ile His Ala Ala Met Gly Gly
                405                 410                 415
Gly Thr Gly Met Asn Leu Phe His Arg Arg Phe Pro Thr Arg Cys Phe
            420                 425                 430
Asp Val Gly Ile Ala Glu Gln His Ala Val Thr Phe Ala Ala Gly Leu
        435                 440                 445
Ala Cys Glu Gly Leu Lys Pro Phe Cys Ala Ile Tyr Ser Ser Phe Met
    450                 455                 460
Gln Arg Ala Tyr Asp Gln Val Val His Asp Val Asp Leu Gln Lys Leu
465                 470                 475                 480
Pro Val Arg Phe Ala Met Asp Arg Ala Gly Leu Val Gly Ala Asp Gly
                485                 490                 495
Pro Thr His Cys Gly Ser Phe Asp Val Thr Phe Met Ala Cys Leu Pro
            500                 505                 510
Asn Met Val Val Met Ala Pro Ser Asp Glu Ala Asp Leu Phe His Met
    515                 520                 525
Val Ala Thr Ala Ala Ile Asn Asp Arg Pro Ser Cys Phe Arg Tyr
530                 535                 540
Pro Arg Gly Asn Gly Ile Gly Val Gln Leu Pro Thr Gly Asn Lys Gly
545                 550                 555                 560
Thr Pro Leu Glu Ile Gly Lys Gly Arg Ile Leu Ile Glu Gly Glu Arg
                565                 570                 575
Val Ala Leu Leu Gly Tyr Gly Ser Ala Val Gln Asn Cys Leu Ala Ala
            580                 585                 590
Ala Ser Leu Val Glu Cys His Gly Leu Arg Leu Thr Val Ala Asp Ala
        595                 600                 605
Arg Phe Cys Lys Pro Leu Asp Arg Ser Leu Ile Arg Ser Leu Ala Lys
    610                 615                 620
Ser His Glu Val Leu Ile Thr Val Glu Glu Gly Ser Ile Gly Gly Phe
625                 630                 635                 640
Gly Ser His Val Ala Gln Phe Met Ala Leu Asp Gly Leu Leu Asp Gly
                645                 650                 655
Lys Leu Lys Trp Arg Pro Ile Val Leu Pro Asp Arg Tyr Ile Asp His
            660                 665                 670
Gly Ser Pro Ala Asp Gln Leu Ser Leu Ala Gly Leu Thr Pro Ser His
        675                 680                 685
Ile Ala Ala Thr Val Phe Asn Val Leu Gly Gln Thr Arg Glu Ala Leu
    690                 695                 700
```

Glu Val Met Ser
705

<210> SEQ ID NO 13
<211> LENGTH: 526
<212> TYPE: DNA
<213> ORGANISM: Triticum aestivum
<220> FEATURE:
<221> NAME/KEY: unsure
<222> LOCATION: (343)
<223> OTHER INFORMATION: n = A, C, G or T
<220> FEATURE:
<221> NAME/KEY: unsure
<222> LOCATION: (349)
<223> OTHER INFORMATION: n = A, C, G or T
<220> FEATURE:
<221> NAME/KEY: unsure
<222> LOCATION: (356)
<223> OTHER INFORMATION: n = A, C, G or T
<220> FEATURE:
<221> NAME/KEY: unsure
<222> LOCATION: (363)
<223> OTHER INFORMATION: n = A, C, G or T
<220> FEATURE:
<221> NAME/KEY: unsure
<222> LOCATION: (374)
<223> OTHER INFORMATION: n = A, C, G or T
<220> FEATURE:
<221> NAME/KEY: unsure
<222> LOCATION: (379)
<223> OTHER INFORMATION: n = A, C, G or T
<220> FEATURE:
<221> NAME/KEY: unsure
<222> LOCATION: (407)
<223> OTHER INFORMATION: n = A, C, G or T
<220> FEATURE:
<221> NAME/KEY: unsure
<222> LOCATION: (413)
<223> OTHER INFORMATION: n = A, C, G or T
<220> FEATURE:
<221> NAME/KEY: unsure
<222> LOCATION: (418)
<223> OTHER INFORMATION: n = A, C, G or T
<220> FEATURE:
<221> NAME/KEY: unsure
<222> LOCATION: (446)
<223> OTHER INFORMATION: n = A, C, G or T
<220> FEATURE:
<221> NAME/KEY: unsure
<222> LOCATION: (456)
<223> OTHER INFORMATION: n = A, C, G or T
<220> FEATURE:
<221> NAME/KEY: unsure
<222> LOCATION: (465)
<223> OTHER INFORMATION: n = A, C, G or T
<220> FEATURE:
<221> NAME/KEY: unsure
<222> LOCATION: (478)
<223> OTHER INFORMATION: n = A, C, G or T
<220> FEATURE:
<221> NAME/KEY: unsure
<222> LOCATION: (502)
<223> OTHER INFORMATION: n = A, C, G or T
<220> FEATURE:
<221> NAME/KEY: unsure
<222> LOCATION: (504)
<223> OTHER INFORMATION: n = A, C, G or T
<220> FEATURE:
<221> NAME/KEY: unsure
<222> LOCATION: (509)
<223> OTHER INFORMATION: n = A, C, G or T
<220> FEATURE:
<221> NAME/KEY: unsure
<222> LOCATION: (513)
<223> OTHER INFORMATION: n = A, C, G or T
<220> FEATURE:
<221> NAME/KEY: unsure
<222> LOCATION: (517)

<223> OTHER INFORMATION: n = A, C, G or T
<220> FEATURE:
<221> NAME/KEY: unsure
<222> LOCATION: (519)
<223> OTHER INFORMATION: n = A, C, G or T

<400> SEQUENCE: 13

```
ttgcaatctt gagaaggagg agaggaaaca atggcgctct cgtcgacctt ctccctcccg    60
cggggcttcc tcggcgtgct gcctcaggag caccatttcg ctcccgccgt cgagctccag   120
gccaagccgc tcaagacgcc gaggaggagg tcgtccggca tttctgcgtc gctgtcggag   180
agggaagcag agtaccactc gcagcggccg ccgacgccgc tgctggacac cgtgaactac   240
cccatccaca tgaagaacct gtccctcaag gagctgcagc agctctccga cgaagctgcg   300
ctccgacgtc atcttccact ctccaagaac ggcgggcaac tcggtcanc ctccgngtcg    360
tcnagctcac gtcncgctng actaactttt caacaaccgc aggacanctc tcnggaantt   420
ggcaacaatc taccgcacaa aatttnacgg ggcggngcat aaatnccaca tgcggagnca   480
aacggacttc cggcttctca ancntccgnc acnatanana gcttct                 526
```

<210> SEQ ID NO 14
<211> LENGTH: 106
<212> TYPE: PRT
<213> ORGANISM: Triticum aestivum
<220> FEATURE:
<221> NAME/KEY: UNSURE
<222> LOCATION: (105)
<223> OTHER INFORMATION: Xaa = ANY AMINO ACID

<400> SEQUENCE: 14

```
Met Ala Leu Ser Ser Thr Phe Ser Leu Pro Arg Gly Phe Leu Gly Val
 1               5                  10                  15
Leu Pro Gln Glu His His Phe Ala Pro Ala Val Glu Leu Gln Ala Lys
            20                  25                  30
Pro Leu Lys Thr Pro Arg Arg Arg Ser Ser Gly Ile Ser Ala Ser Leu
        35                  40                  45
Ser Glu Arg Glu Ala Glu Tyr His Ser Gln Arg Pro Pro Thr Pro Leu
    50                  55                  60
Leu Asp Thr Val Asn Tyr Pro Ile His Met Lys Asn Leu Ser Leu Lys
65                  70                  75                  80
Glu Leu Gln Gln Leu Ser Asp Glu Ala Ala Leu Arg Arg His Leu Pro
                85                  90                  95
Leu Ser Lys Asn Gly Gly Gln Leu Xaa Ser
            100                 105
```

<210> SEQ ID NO 15
<211> LENGTH: 640
<212> TYPE: DNA
<213> ORGANISM: Triticum aestivum
<220> FEATURE:
<221> NAME/KEY: unsure
<222> LOCATION: (378)
<223> OTHER INFORMATION: n = A, C, G or T
<220> FEATURE:
<221> NAME/KEY: unsure
<222> LOCATION: (394)
<223> OTHER INFORMATION: n = A, C, G or T
<220> FEATURE:
<221> NAME/KEY: unsure
<222> LOCATION: (458)
<223> OTHER INFORMATION: n = A, C, G or T
<220> FEATURE:
<221> NAME/KEY: unsure
<222> LOCATION: (502)

```
<223> OTHER INFORMATION: n = A, C, G or T
<220> FEATURE:
<221> NAME/KEY: unsure
<222> LOCATION: (513)
<223> OTHER INFORMATION: n = A, C, G or T
<220> FEATURE:
<221> NAME/KEY: unsure
<222> LOCATION: (536)
<223> OTHER INFORMATION: n = A, C, G or T
<220> FEATURE:
<221> NAME/KEY: unsure
<222> LOCATION: (584)
<223> OTHER INFORMATION: n = A, C, G or T
<220> FEATURE:
<221> NAME/KEY: unsure
<222> LOCATION: (600)
<223> OTHER INFORMATION: n = A, C, G or T
<220> FEATURE:
<221> NAME/KEY: unsure
<222> LOCATION: (608)
<223> OTHER INFORMATION: n = A, C, G or T
<220> FEATURE:
<221> NAME/KEY: unsure
<222> LOCATION: (614)
<223> OTHER INFORMATION: n = A, C, G or T

<400> SEQUENCE: 15
ggccttcgac gtggcgttca tggcgtgcct ccccaacatg gtcgtcatgg ccccgtccga    60
cgaggccgag ctgctgaaca tggtcgccac cgccgcggcc atcgacgacc gcccctcgtg   120
cttccgctat ccgaggggca acggcatcgg cgtcccgttg ccggaaaact acaaaggcac   180
tgccatcgag gtcggcaaag gcaggatcat gatcgagggc gagagggtgg cgctgctggg   240
gtacgggtcg gcggtgcagt actgcatggc cgcctcgtcc atcgtggcgc aacacggcct   300
cagggtcacc gtcgccgacg ccaggttctg caagccgttg gaccacgccc tcatcaagag   360
cctcgccaag tccacgangt gatcatcaac gtcnaggaag ctcatcggcg gcttcgctca   420
cacgtggcta attcatggcc tggacggctt ctcaacgnaa actaagtggc ggcggtggtg   480
tcccgacaag tcatcacatg gntaccgcga tanctgtgga ggcggctacc cgtganatgc   540
gcacgtgtaa atctgggaag aaaaaagctc catatacgtc aatncaaaca ttgtgctcan   600
aaaacttnat tgcntaggta aaatatcgta aatattctta                         640

<210> SEQ ID NO 16
<211> LENGTH: 124
<212> TYPE: PRT
<213> ORGANISM: Triticum aestivum

<400> SEQUENCE: 16

Ala Phe Asp Val Ala Phe Met Ala Cys Leu Pro Asn Met Val Met
 1               5                  10                  15

Ala Pro Ser Asp Glu Ala Glu Leu Leu Asn Met Val Ala Thr Ala Ala
                20                  25                  30

Ala Ile Asp Asp Arg Pro Ser Cys Phe Arg Tyr Pro Arg Gly Asn Gly
            35                  40                  45

Ile Gly Val Pro Leu Pro Glu Asn Tyr Lys Gly Thr Ala Ile Glu Val
        50                  55                  60

Gly Lys Gly Arg Ile Met Ile Glu Gly Glu Arg Val Ala Leu Leu Gly
65                  70                  75                  80

Tyr Gly Ser Ala Val Gln Tyr Cys Met Ala Ala Ser Ser Ile Val Ala
                85                  90                  95

Gln His Gly Leu Arg Val Thr Val Ala Asp Ala Arg Phe Cys Lys Pro
            100                 105                 110
```

Leu Asp His Ala Leu Ile Lys Ser Leu Ala Lys Ser
         115                 120

<210> SEQ ID NO 17
<211> LENGTH: 1365
<212> TYPE: DNA
<213> ORGANISM: Zea mays

<400> SEQUENCE: 17

```
gagaatgaca agcgcattgt ggtagttcat ggcggcatgg gaatcgatcg atcactccgc     60
ttattccagt ccaggttccc agacagattt tttgacttgg gcatcgctga gcaacatgct    120
gttacctttt ctgctggttt ggcctgcgga ggtctaaagc ctttctgcat aattccatcc    180
acatttcttc agcgagcata tgatcagata attgaagatg tggacatgca aaagatacca    240
gttcgttttg ctatcacaaa tgctggtctg gtaggatctg agggtccaac taattcagga    300
ccatttgata ttacattcat gtcatgcttg ccaaacatga ttgtcatgtc accatctaat    360
gaggatgaac ttattgacat ggtggcaaca gctgcaatga ttgaggacag acctatttgc    420
ttccgctatc ctaggggtgc cattgttggg actagtggaa gtgtaacata tgggaatcca    480
tttgagattg gtaaaggaga gattcttgtc gagggaaaag agatagcttt tcttggctat    540
ggcgaggtgg tccagagatg cttgattgct cgatctcttt tatccaactt tggtattcag    600
gcgacagttg caaacgcgag gttttgcaag ccgcttgaca tcgacctaat cagaacgctg    660
tgtcagcagc atagttttct tatcacagtg gaagaaggaa cggttggtgg ctttggatca    720
cacgtctcac agtttatttc tctcgatggt ctacttgacg gtcgaacaaa ggttcccgtt    780
tcttttgtaac tctgcagtgg cgacccattg tgctgccaga caggtacatt gagcatgcat    840
cgctcgcaga gcaacttgac ctggctggcc taactgccca tcacatagct gcaactgcat    900
tgaccctcct agggcgtcat cgtgatgccc ttctgttgat gaagtagggg aagggaccac    960
caagaagaat ggaattggat agataaaagg caatatgtgc agaagttgat tcggaggacg   1020
ctcatcatgc tgttttacga ttgtgttgtc tggatagaac tgaagcgtgc cgtgggaggt   1080
ggccaaatgc acaaatccca agagggacg acaaagccta tagcaccata gattaatagt   1140
cacggtgtat atactgaaaa gaatttacag accaccgatg taacgttgtt actgtgcatg   1200
ttaatactga aattgtggta agacgccaac tgggagaatg agctagagct gccatgtttc   1260
agttaatgta ataaagctac ttagttttgt atgtaccaat tcattcctta atgttggaat   1320
tcataaccct agcgttcacc tcaaaaaaaa aaaaaaaaaa aaaaa                    1365
```

<210> SEQ ID NO 18
<211> LENGTH: 262
<212> TYPE: PRT
<213> ORGANISM: Zea mays

<400> SEQUENCE: 18

Glu Asn Asp Lys Arg Ile Val Val His Gly Gly Met Gly Ile Asp
 1               5                  10                  15

Arg Ser Leu Arg Leu Phe Gln Ser Arg Phe Pro Asp Arg Phe Phe Asp
                20                  25                  30

Leu Gly Ile Ala Glu Gln His Ala Val Thr Phe Ser Ala Gly Leu Ala
            35                  40                  45

Cys Gly Gly Leu Lys Pro Phe Cys Ile Ile Pro Ser Thr Phe Leu Gln
        50                  55                  60

Arg Ala Tyr Asp Gln Ile Ile Glu Asp Val Asp Met Gln Lys Ile Pro
65                  70                  75                  80

```
Val Arg Phe Ala Ile Thr Asn Ala Gly Leu Val Gly Ser Glu Gly Pro
                 85                  90                  95

Thr Asn Ser Gly Pro Phe Asp Ile Thr Phe Met Ser Cys Leu Pro Asn
            100                 105                 110

Met Ile Val Met Ser Pro Ser Asn Glu Asp Glu Leu Ile Asp Met Val
        115                 120                 125

Ala Thr Ala Ala Met Ile Glu Asp Arg Pro Ile Cys Phe Arg Tyr Pro
    130                 135                 140

Arg Gly Ala Ile Val Gly Thr Ser Gly Ser Val Thr Tyr Gly Asn Pro
145                 150                 155                 160

Phe Glu Ile Gly Lys Gly Glu Ile Leu Val Glu Gly Lys Glu Ile Ala
                165                 170                 175

Phe Leu Gly Tyr Gly Glu Val Val Gln Arg Cys Leu Ile Ala Arg Ser
            180                 185                 190

Leu Leu Ser Asn Phe Gly Ile Gln Ala Thr Val Ala Asn Ala Arg Phe
        195                 200                 205

Cys Lys Pro Leu Asp Ile Asp Leu Ile Arg Thr Leu Cys Gln Gln His
    210                 215                 220

Ser Phe Leu Ile Thr Val Glu Glu Gly Thr Val Gly Phe Gly Ser
225                 230                 235                 240

His Val Ser Gln Phe Ile Ser Leu Asp Gly Leu Leu Asp Gly Arg Thr
                245                 250                 255

Lys Val Pro Val Ser Leu
                260

<210> SEQ ID NO 19
<211> LENGTH: 1488
<212> TYPE: DNA
<213> ORGANISM: Zea mays

<400> SEQUENCE: 19
ggcacgagag cagatcggtg gctcagtgca cgagctggcg gcgaaggtgg acgagtacgc      60
ccgcggcatg atcagcgggc ccggctcctc gctcttcgag gagctcggtc tctactacat     120
cggccccgtc gacggccaca acatcgacga cctcatcacc atcctcaacg acgtcaagag     180
caccaagacc accggccccg tcctcatcca cgtcgtcacc gagaagggcc gcggctaccc     240
ctacgccgag cgagccgccg acaagtacca cggtgtcgcc aagtttgatc cggcgaccgg     300
gaagcagttc aagtccccgg ccaagacgct gtcctacacc aactacttcg ccgaggcgct     360
catcgccgag gcggagcagg acagcaagat cgtggccatc cacgcggcca tgggcggcgg     420
cacgggctc aactacttcc tccgccgctt cccgagccgg tgcttcgacg tcgggatcgc     480
ggagcagcac gccgtcacgt cgcggccgg cctggcctgc gagggcctca gcccttctg     540
cgccatctac tcgtctttcc tgcagcgcgc ctacgaccag gtcgtgcacg acgtcgatct     600
gcagaagcta ccggtgcggt cgccatgga cagggccggg ctggtcggcg cggacgggcc     660
gacccactgc ggtgcgttcg acgtcgcgta catggcctgc ctgcccaaca tggtcgtcat     720
ggccccgtcc gacgaggccg agctctgcca catggtcgcc accgccgcgg ccatcgacga     780
ccgcccgtcc tgcttccgct acccgagagg caacggcgtt ggcgtcccgt tgccgcccaa     840
ctacaaaggc actcccctcg aggtcggcaa aggcaggatc ctgcttgagg gcgaccgggt     900
ggcgctgctg gggtacgggt cggcagtgca gtactgcctg actgccgcgt ccctggtgca     960
gcgccacggc ctcaaggtca ccgtcgccga cgcgaggttc tgcaagccgc tggaccacgc    1020
```

```
cctgatcagg agcctggcca agtcccacga ggtgctcatc accgtggagg aaggctccat    1080
cggcgggttc ggctcgcacg tcgcccagtt catgggcctg acggccttc tcgacggcaa     1140 actcaagtgg cgaccgctgg tgcttcctga caggtacatc gaccatggat cgccggccga    1200
tcagctggcc gaggctgggc tgacgccgtc acacatcgcc gcgtcggtgt tcaacatcct    1260
ggggcagaac agggaggctc ttgccatcat ggcagtgcca aacgcgtaga acttgtgctg    1320
atctgggcct atagagatga ttgtacattt tgtcgttaac tagagtgtct gaacttggga    1380
gattagtctt ctttggatga aagtgtcgcc ggaacaacag ttaccgtttc ttttttgaa     1440 agagaaaggc aaaagatttg ccattccaat aaaaaaaaaa aaaaaaaa                 1488
```

<210> SEQ ID NO 20
<211> LENGTH: 435
<212> TYPE: PRT
<213> ORGANISM: Zea mays

<400> SEQUENCE: 20

```
Ala Arg Glu Gln Ile Gly Gly Ser Val His Glu Leu Ala Ala Lys Val
  1               5                  10                  15

Asp Glu Tyr Ala Arg Gly Met Ile Ser Gly Pro Gly Ser Ser Leu Phe
             20                  25                  30

Glu Glu Leu Gly Leu Tyr Tyr Ile Gly Pro Val Asp Gly His Asn Ile
         35                  40                  45

Asp Asp Leu Ile Thr Ile Leu Asn Asp Val Lys Ser Thr Lys Thr Thr
     50                  55                  60

Gly Pro Val Leu Ile His Val Val Thr Glu Lys Gly Arg Gly Tyr Pro
 65                  70                  75                  80

Tyr Ala Glu Arg Ala Ala Asp Lys Tyr His Gly Val Ala Lys Phe Asp
                 85                  90                  95

Pro Ala Thr Gly Lys Gln Phe Lys Ser Pro Ala Lys Thr Leu Ser Tyr
            100                 105                 110

Thr Asn Tyr Phe Ala Glu Ala Leu Ile Ala Glu Ala Glu Gln Asp Ser
        115                 120                 125

Lys Ile Val Ala Ile His Ala Ala Met Gly Gly Thr Gly Leu Asn
    130                 135                 140

Tyr Phe Leu Arg Arg Phe Pro Ser Arg Cys Phe Asp Val Gly Ile Ala
145                 150                 155                 160

Glu Gln His Ala Val Thr Phe Ala Ala Gly Leu Ala Cys Glu Gly Leu
                165                 170                 175

Lys Pro Phe Cys Ala Ile Tyr Ser Ser Phe Leu Gln Arg Gly Tyr Asp
            180                 185                 190

Gln Val Val His Asp Val Asp Leu Gln Lys Leu Pro Val Arg Phe Ala
        195                 200                 205

Met Asp Arg Ala Gly Leu Val Gly Ala Asp Gly Pro Thr His Cys Gly
    210                 215                 220

Ala Phe Asp Val Ala Tyr Met Ala Cys Leu Pro Asn Met Val Val Met
225                 230                 235                 240

Ala Pro Ser Asp Glu Ala Glu Leu Cys His Met Val Ala Thr Ala Ala
                245                 250                 255

Ala Ile Asp Asp Arg Pro Ser Cys Phe Arg Tyr Pro Arg Gly Asn Gly
            260                 265                 270

Val Gly Val Pro Leu Pro Pro Asn Tyr Lys Gly Thr Pro Leu Glu Val
        275                 280                 285

Gly Lys Gly Arg Ile Leu Leu Glu Gly Asp Arg Val Ala Leu Leu Gly
```

-continued

```
        290                 295                 300
Tyr Gly Ser Ala Val Gln Tyr Cys Leu Thr Ala Ala Ser Leu Val Gln
305                 310                 315                 320

Arg His Gly Leu Lys Val Thr Val Ala Asp Ala Arg Phe Cys Lys Pro
                325                 330                 335

Leu Asp His Ala Leu Ile Arg Ser Leu Ala Lys Ser His Glu Val Leu
                340                 345                 350

Ile Thr Val Glu Glu Gly Ser Ile Gly Gly Phe Gly Ser His Val Ala
                355                 360                 365

Gln Phe Met Ala Leu Asp Gly Leu Leu Asp Gly Lys Leu Lys Trp Arg
370                 375                 380

Pro Leu Val Leu Pro Asp Arg Tyr Ile Asp His Gly Ser Pro Ala Asp
385                 390                 395                 400

Gln Leu Ala Glu Ala Gly Leu Thr Pro Ser His Ile Ala Ala Ser Val
                405                 410                 415

Phe Asn Ile Leu Gly Gln Asn Arg Glu Ala Leu Ala Ile Met Ala Val
                420                 425                 430

Pro Asn Ala
        435
```

<210> SEQ ID NO 21
<211> LENGTH: 461
<212> TYPE: DNA
<213> ORGANISM: Zea mays

<400> SEQUENCE: 21

```
gagccggcgg cggcggccac gtcgtcggga ccgtggaaga tcgacttctc cggcgagaag      60
ccgccgacgc cgctgctgga caccgtgaac tacccgctcc acatgaagaa cctgtcgatc     120
ttggagctgg agcagctggc ggcggagctc cgcgcggagg tcgtgcacac cgtgtccaag     180
accggcgggc acctgagctc cagcctgggc gttgtggagc tgtcggtggc gctgcaccac     240
gtgttcgaca ccccggagga caagatcatc tgggacgtgg gccaccaggc gtacccgcac     300
aagatcctga cggggcggcg gtcgcggatg cacaccatcc gccagacctc cgggctggcg     360
gggttcccca gcgcgacga gagcgcgcac gacgcgttcg ggtcggcca cagctccaac      420
agcatctcgg cggcgctggg catggccgtt gcgcgggacc t                         461
```

<210> SEQ ID NO 22
<211> LENGTH: 153
<212> TYPE: PRT
<213> ORGANISM: Zea mays

<400> SEQUENCE: 22

```
Glu Pro Ala Ala Ala Thr Ser Ser Gly Pro Trp Lys Ile Asp Phe
  1               5                  10                  15

Ser Gly Glu Lys Pro Pro Thr Pro Leu Leu Asp Thr Val Asn Tyr Pro
                20                  25                  30

Leu His Met Lys Asn Leu Ser Ile Leu Glu Leu Glu Gln Leu Ala Ala
                35                  40                  45

Glu Leu Arg Ala Glu Val Val His Thr Val Ser Lys Thr Gly Gly His
        50                  55                  60

Leu Ser Ser Ser Leu Gly Val Val Glu Leu Ser Val Ala Leu His His
65                  70                  75                  80

Val Phe Asp Thr Pro Glu Asp Lys Ile Ile Trp Asp Val Gly His Gln
                85                  90                  95
```

Ala Tyr Pro His Lys Ile Leu Thr Gly Arg Arg Ser Arg Met His Thr
            100                 105                 110

Ile Arg Gln Thr Ser Gly Leu Ala Gly Phe Pro Lys Arg Asp Glu Ser
        115                 120                 125

Ala His Asp Ala Phe Gly Val Gly His Ser Ser Asn Ser Ile Ser Ala
    130                 135                 140

Ala Leu Gly Met Ala Val Ala Arg Asp
145                 150

<210> SEQ ID NO 23
<211> LENGTH: 698
<212> TYPE: DNA
<213> ORGANISM: Zea mays
<220> FEATURE:
<221> NAME/KEY: unsure
<222> LOCATION: (418)
<223> OTHER INFORMATION: n = A, C, G or T
<220> FEATURE:
<221> NAME/KEY: unsure
<222> LOCATION: (453)
<223> OTHER INFORMATION: n = A, C, G or T
<220> FEATURE:
<221> NAME/KEY: unsure
<222> LOCATION: (476)
<223> OTHER INFORMATION: n = A, C, G or T
<220> FEATURE:
<221> NAME/KEY: unsure
<222> LOCATION: (509)
<223> OTHER INFORMATION: n = A, C, G or T
<220> FEATURE:
<221> NAME/KEY: unsure
<222> LOCATION: (580)
<223> OTHER INFORMATION: n = A, C, G or T
<220> FEATURE:
<221> NAME/KEY: unsure
<222> LOCATION: (596)..(597)
<223> OTHER INFORMATION: n = A, C, G or T
<220> FEATURE:
<221> NAME/KEY: unsure
<222> LOCATION: (663)
<223> OTHER INFORMATION: n = A, C, G or T
<220> FEATURE:
<221> NAME/KEY: unsure
<222> LOCATION: (672)
<223> OTHER INFORMATION: n = A, C, G or T
<220> FEATURE:
<221> NAME/KEY: unsure
<222> LOCATION: (674)..(675)
<223> OTHER INFORMATION: n = A, C, G or T
<220> FEATURE:
<221> NAME/KEY: unsure
<222> LOCATION: (692)
<223> OTHER INFORMATION: n = A, C, G or T

<400> SEQUENCE: 23
gagcgcgacg ccctgccagt agccgccgca accggccgcc ggtcccgcgc gaggggagga      60
ggagatcact gcggcggcgt cttctgccgg tttgaggatt cggggcatca ctgcagcagc    120
tggcgccagg ctccagcatg gacacggcgt tctgagtcc tccgcttgcc cgtaatctgg     180
tttatgacga gtttgccgtt cttcaccca ctagctaccc ttttcatact cttcggtatt     240
tgagatgcaa tccaatgtat tcgagaccgc tgctaacaat agcaccagcc tcaccatcaa    300
ggggcttgat tcagagagtg gccgcactac ctgatgttga tgatttcttc tgggagaagg    360
atcctactcc aatacttgac acaattgatg cacccattca tttgaaaaat ctatctanag    420
ctcaaagcag ttagcccgat gaagtttgtt canaaatag ctttcataat tgtcanaaaa     480
tgccaacccg tgtggtgctg atcgctcant tgtggagctg acaattgcta tacattatgt    540
gttcaatgcc ccaatggata agaaactatg ggatgctggn caaacatgca tatgcnnaca    600

```
agattcttac aaggaaggcg ctcttctctt ccattctatt acacagaaaa aatggccttt      660
ctnggtttaa cntnncgttt ttgataaccg antatgat                              698

<210> SEQ ID NO 24
<211> LENGTH: 35
<212> TYPE: PRT
<213> ORGANISM: Zea mays

<400> SEQUENCE: 24

Gln Arg Val Ala Ala Leu Pro Asp Val Asp Asp Phe Phe Trp Glu Lys
  1               5                  10                  15

Asp Pro Thr Pro Ile Leu Asp Thr Ile Asp Ala Pro Ile His Leu Lys
             20                  25                  30

Asn Leu Ser
         35

<210> SEQ ID NO 25
<211> LENGTH: 2618
<212> TYPE: DNA
<213> ORGANISM: Oryza sativa

<400> SEQUENCE: 25
gcacgagctt acatgtcctt tctccacctc ggtggtcatc agctagacag ctatcgcgcg       60
ccgtcccacc accatcttgc tccactacgc ggaccaccgc gcgcgagcag agcatctcct      120
cactctctag cttgctccag tttcgcgtag ctgcgtgaca gttcaattga actctctgga      180
ttcgttggtt acttcgtctg agctgctgca gcgttgagga ggaggaggag caatggcgct      240
cacgacgttc tccatttcga gaggaggctt cgtcggcgcg ctgccgcagg agggcattt       300 cgctccggcg gcggcggagc tcagtctcca caagctccag agcaggccac acaaggctag      360
gcggaggtcg tcgtcgagca tctcggcgtc gctgtccacg gagagggagg cggcggagta      420
ccactcgcag cggccaccga cgccgctgct ggacacggtc aactacccca tccacatgaa      480
gaacctgtcc ctcaaggagc tccagcagct cgccgacgag ctccgctccg acgtcatctt      540
ccacgtctcc aagaccgggg gacatctcgg gtccagcctc ggcgtcgtcg agctcaccgt      600
cgcgctccac tacgtgttca acacgcctca ggacaagatc ctctgggacg tcggccacca      660
gtcgtaccct cacaagattc tgaccgggcg gcgcgacaag atgccgacga tgcgtcagac      720
caacggcttg tcgggattca ccaagcggtc ggagagcgag tacgactcct tcggcaccgg      780
ccacagctcc accaccatct ccgccgccct cgggatggcg gtggggaggg atctcaaggg      840
agggaagaac aacgtggtgg cggtgatcgc cgacggcgcc atgacggccg gcaggcgta      900 cgaggcgatg aataacgcgg ggtatctcga ctccgatatg atcgtgattc tcaacgacaa      960
caagcaggtg tcgctgccga cggcgacgct cgacgggccg gcgccgccgg tgggcgcgct     1020
cagcagcgcc ctcagcaagc tgcagtccag ccgcccactc agggagctca gggaggtggc     1080
aaagggcgtg acgaagcaaa tcgagggtc ggtgcacgag ctggcggcga aggtggacga     1140
gtacgcccgc ggcatgatca gcggctccgg ctcgacgctc ttcgaggagc tcggcctcta     1200
ctacatcggc cccgtcgacg gccacaacat cgacgacctc atcaccatcc tccgcgaggt     1260
caagagcacc aagaccacag gcccggtgct catcccacgtc gtcaccgaga aggccgcgg     1320 ctaccctac gccgagcgcg ccgccgacaa gtaccacggc gtggcgaagt cgatccggc      1380 gacggggaag cagttcaagt cgccggcgaa gacgctgtcg tacacgaact acttcgcgga     1440
ggcgctcatc gccgaggcgg agcaggacaa caggtcgtg gccatccacg cggccatggg     1500
```

-continued

```
gggaggcacg gggctcaact acttcctccg ccgcttcccg aaccggtgct tcgacgtcgg   1560
gatcgccgag cagcacgccg tcacgttcgc cgccggcctc gcctgcgagg gcctcaagcc   1620
gttctgcgcc atctactcct ccttcctgca gagaggctac gaccaggtgg tgcacgacgt   1680
ggacctccag aagctgccgg tgaggttcgc catggacagg gccgggctcg tgggcgccga   1740
cgggccgacg cactgcggcg cgttcgacgt cacctacatg gcgtgcctgc cgaacatggt   1800
cgtcatggcc ccgtccgacg aggcggagct ctgccacatg gtcgccaccg ccgcggccat   1860
cgacgaccgc ccctcctgct tccgctaccc aagaggcaac ggcatcggcg tcccgctacc   1920
acccaactac aaaggcgttc ccctcgaggt aggcaaaggg agggtactgc tggagggcga   1980
gagggtggcg ctgcttgggt acggttcggc ggtgcagtac tgcctcgccg cagcgtcgct   2040
ggtggagcgg cacggcctca aggtgaccgt cgccgacgcg aggttctgca gccgctgga   2100 ccaaacgctc atcaggaggc tggccagctc ccacgaggtg ctcctcaccg tcgaggaagg   2160
ctccatcggc gggttcggct cccacgtcgc gcagttcatg gccctcgacg gcctcctcga   2220
cggcaaactc aagtggcggc cgctggtgct acccgacagg tacatcgacc acgggtcacc   2280
ggcggatcag ctggcggagg cagggctgac gccgtcgcac atcgcggcga cggtgttcaa   2340
cgtgctgggc caggcgaggg aggcgctcgc catcatgacg gtgcccaacg cgtagcagat   2400
gcgtggcgcc tctggtagag acaatgcttt gtacatgtag agatcagtga attgtatatt   2460
agtcggcgtc gggataaata ttgattagtg atgctgaggg gaacagttac agttttttg   2520 ctcttcagtt gttcgtggac ggagacccgg ctgctcgatg ttcgatcgct tgtatatcta   2580
agaaatgttg taagtggata aaaaaaaaaa aaaaaaa                           2618
```

<210> SEQ ID NO 26
<211> LENGTH: 720
<212> TYPE: PRT
<213> ORGANISM: Oryza sativa

<400> SEQUENCE: 26

```
Met Ala Leu Thr Thr Phe Ser Ile Ser Arg Gly Gly Phe Val Gly Ala
  1               5                  10                  15

Leu Pro Gln Glu Gly His Phe Ala Pro Ala Ala Glu Leu Ser Leu
                 20                  25                  30

His Lys Leu Gln Ser Arg Pro His Lys Ala Arg Arg Ser Ser Ser
             35                  40                  45

Ser Ile Ser Ala Ser Leu Ser Thr Glu Arg Glu Ala Ala Glu Tyr His
 50                  55                  60

Ser Gln Arg Pro Pro Thr Pro Leu Leu Asp Thr Val Asn Tyr Pro Ile
 65                  70                  75                  80

His Met Lys Asn Leu Ser Leu Lys Glu Leu Gln Gln Leu Ala Asp Glu
                 85                  90                  95

Leu Arg Ser Asp Val Ile Phe His Val Ser Lys Thr Gly Gly His Leu
                100                 105                 110

Gly Ser Ser Leu Gly Val Val Glu Leu Thr Val Ala Leu His Tyr Val
            115                 120                 125

Phe Asn Thr Pro Gln Asp Lys Ile Leu Trp Asp Val Gly His Gln Ser
        130                 135                 140

Tyr Pro His Lys Ile Leu Thr Gly Arg Arg Asp Lys Met Pro Thr Met
145                 150                 155                 160

Arg Gln Thr Asn Gly Leu Ser Gly Phe Thr Lys Arg Ser Glu Ser Glu
                165                 170                 175
```

```
Tyr Asp Ser Phe Gly Thr Gly His Ser Ser Thr Ile Ser Ala Ala
        180                 185                 190

Leu Gly Met Ala Val Gly Arg Asp Leu Lys Gly Gly Lys Asn Asn Val
            195                 200                 205

Val Ala Val Ile Gly Asp Gly Ala Met Thr Ala Gly Gln Ala Tyr Glu
        210                 215                 220

Ala Met Asn Asn Ala Gly Tyr Leu Asp Ser Asp Met Ile Val Ile Leu
225                 230                 235                 240

Asn Asp Asn Lys Gln Val Ser Leu Pro Thr Ala Thr Leu Asp Gly Pro
                245                 250                 255

Ala Pro Pro Val Gly Ala Leu Ser Ser Ala Leu Ser Lys Leu Gln Ser
            260                 265                 270

Ser Arg Pro Leu Arg Glu Leu Arg Glu Val Ala Lys Gly Val Thr Lys
        275                 280                 285

Gln Ile Gly Gly Ser Val His Glu Leu Ala Ala Lys Val Asp Glu Tyr
    290                 295                 300

Ala Arg Gly Met Ile Ser Gly Ser Gly Ser Thr Leu Phe Glu Glu Leu
305                 310                 315                 320

Gly Leu Tyr Tyr Ile Gly Pro Val Asp Gly His Asn Ile Asp Asp Leu
                325                 330                 335

Ile Thr Ile Leu Arg Glu Val Lys Ser Thr Lys Thr Thr Gly Pro Val
            340                 345                 350

Leu Ile His Val Val Thr Glu Lys Gly Arg Gly Tyr Pro Tyr Ala Glu
        355                 360                 365

Arg Ala Ala Asp Lys Tyr His Gly Val Ala Lys Phe Asp Pro Ala Thr
370                 375                 380

Gly Lys Gln Phe Lys Ser Pro Ala Lys Thr Leu Ser Tyr Thr Asn Tyr
385                 390                 395                 400

Phe Ala Glu Ala Leu Ile Ala Glu Ala Glu Gln Asp Asn Arg Val Val
                405                 410                 415

Ala Ile His Ala Ala Met Gly Gly Gly Thr Gly Leu Asn Tyr Phe Leu
            420                 425                 430

Arg Arg Phe Pro Asn Arg Cys Phe Asp Val Gly Ile Ala Glu Gln His
        435                 440                 445

Ala Val Thr Phe Ala Ala Gly Leu Ala Cys Glu Gly Leu Lys Pro Phe
    450                 455                 460

Cys Ala Ile Tyr Ser Ser Phe Leu Gln Arg Gly Tyr Asp Gln Val Val
465                 470                 475                 480

His Asp Val Asp Leu Gln Lys Leu Pro Val Arg Phe Ala Met Asp Arg
                485                 490                 495

Ala Gly Leu Val Gly Ala Asp Gly Pro Thr His Cys Gly Ala Phe Asp
            500                 505                 510

Val Thr Tyr Met Ala Cys Leu Pro Asn Met Val Val Met Ala Pro Ser
        515                 520                 525

Asp Glu Ala Glu Leu Cys His Met Val Ala Thr Ala Ala Ala Ile Asp
530                 535                 540

Asp Arg Pro Ser Cys Phe Arg Tyr Pro Arg Gly Asn Gly Ile Gly Val
545                 550                 555                 560

Pro Leu Pro Pro Asn Tyr Lys Gly Val Pro Leu Glu Val Gly Lys Gly
                565                 570                 575

Arg Val Leu Leu Glu Gly Glu Arg Val Ala Leu Leu Gly Tyr Gly Ser
            580                 585                 590
```

-continued

```
Ala Val Gln Tyr Cys Leu Ala Ala Ala Ser Leu Val Glu Arg His Gly
            595                 600                 605

Leu Lys Val Thr Val Ala Asp Ala Arg Phe Cys Lys Pro Leu Asp Gln
        610                 615                 620

Thr Leu Ile Arg Arg Leu Ala Ser Ser His Glu Val Leu Leu Thr Val
625                 630                 635                 640

Glu Glu Gly Ser Ile Gly Gly Phe Gly Ser His Val Ala Gln Phe Met
                645                 650                 655

Ala Leu Asp Gly Leu Leu Asp Gly Lys Leu Lys Trp Arg Pro Leu Val
            660                 665                 670

Leu Pro Asp Arg Tyr Ile Asp His Gly Ser Pro Ala Asp Gln Leu Ala
        675                 680                 685

Glu Ala Gly Leu Thr Pro Ser His Ile Ala Ala Thr Val Phe Asn Val
    690                 695                 700

Leu Gly Gln Ala Arg Glu Ala Leu Ala Ile Met Thr Val Pro Asn Ala
705                 710                 715                 720
```

<210> SEQ ID NO 27
<211> LENGTH: 1991
<212> TYPE: DNA
<213> ORGANISM: Oryza sativa

<400> SEQUENCE: 27

```
gcacgaggct ggtcagcata catatgcaca caagattctc acaggaaggc gctcactctt      60
tcatactatt aagcaaagaa aggggctttc aggtttcaca tcccgtttcg agagcgaata     120
tgatcccttt ggtgcaggac atggatgcaa tagtctctcc gcaggccttg ggatggcagt     180
cgcaagggat ctaggtggga ggaaaaaccg aatagtaaca gttataagta actggacaac     240
tatggctggt caggtgtatg aggcaatggg tcatgccggt ttccttgatt ctaacatggt     300
agtgatttta aatgacagcc ggcacacctt gcttcctaaa gcagatagcc aatcaaagat     360
gtctattaat gccctctcta gtgctctgag caaggttcaa tccagcaaag gatttagaaa     420
gtttagggag ctgcaaaagg acttttccaa atggtttggt aaagggatgc atgaatttgc     480
tgccaaaatt gatgagtatg cccgtggtat gataggtcct catggagcaa ctcttttga      540
agaacttgga taatattata ttgggcctat tgatgggaat aacattgatg atctcatttg     600
tgtactcaag gaggtttcta ctctagattc taccggccca gtacttgtgc atgtaatcac     660
tgagaatgaa aaagactcag gtggagaatt aatagtgag attactcccg acgaggaagg      720
gcctccagac tcaagccaag acattctaaa gttttttagaa aatggtcttt ctaggacata    780
taatgattgc tttgtagaat cactaatagc agaagcagag aatgacaagc atattgtggt     840
ggttcatgga ggcatgggaa tagatcgatc aatccaatta tttcagtcca gatttccgga     900
cagatttttc gatttgggta cgccgagca acatgctgtt acgttttctg ctggtttggc      960
atgcggaggc ttaaagcctt tctgcataat tccatccacc tttctccagc gagcatatga    1020
tcagatagtc gaagatgtgg acatgcaaaa gataccagtt cgctttgcaa tcacaagtgc    1080
aggtctggtg ggatctgaag gcccgactaa ctcaggacca tttgatatta cattcatgtc    1140
atgcctgcca acatgatcg tcatgtcacc atctaatgag gatgaactta ttgacatggt    1200
ggcaacagct gcaatggttg aggacagacc catttgcttc cggtatccca agggtgccat    1260
cgttgggact agtggcactt tagcatatgg gaatccactt gagattggta aggagagat    1320
tcttgctgag gggaaagaga tagctttttct tggttatggt gatgtggtcc agagatgctt    1380
gatagctcga tctcttctgt tcaactttgg catccaggca actgttgcta atgcgagatt    1440
```

```
ttgcaagcca cttgacattg atctgataag aatgttgtgc cagcaacacg atttcctaat    1500
caccgtggaa gaaggaacgg ttggtggttt tggctcacac gtctcgcaat ttatttcact    1560
cgatgggttg cttgatggca aaataaagtg gcgacccatt gtactaccag acaggtacat    1620
cgaacacgct tcgctcacag agcagctcga catggctggg ttgactgctc atcacatcgc    1680
agcaaccgca ctgacccttt tagggcgaca ccgagacgca cttttgttga tgaagtaaga    1740
aggaaaaatg agctagaaaa gaatgaaaag ttgtgcagca agtttgagct ggtagaagac    1800
agccaaattg ctgtttcatg gatattcttc agtctttcag aggaaactga gattgccatg    1860
gcagatacag cctgtgtgca ccactgaaag agcttgcaag tttttatctg tgctccagat    1920
gcttactgta atctgttcat gggggctgta catactataa accctgtttt gatgatgatt    1980
atgttaatgt t                                                         1991
```

<210> SEQ ID NO 28
<211> LENGTH: 578
<212> TYPE: PRT
<213> ORGANISM: Oryza sativa
<220> FEATURE:
<221> NAME/KEY: UNSURE
<222> LOCATION: (184)
<223> OTHER INFORMATION: Xaa = ANY AMINO ACID

<400> SEQUENCE: 28

```
His Glu Ala Gly Gln His Thr Tyr Ala His Lys Ile Leu Thr Gly Arg
 1               5                  10                  15

Arg Ser Leu Phe His Thr Ile Lys Gln Arg Lys Gly Leu Ser Gly Phe
            20                  25                  30

Thr Ser Arg Phe Glu Ser Glu Tyr Asp Pro Phe Gly Ala Gly His Gly
        35                  40                  45

Cys Asn Ser Leu Ser Ala Gly Leu Gly Met Ala Val Ala Arg Asp Leu
    50                  55                  60

Gly Gly Arg Lys Asn Arg Ile Val Thr Val Ile Ser Asn Trp Thr Thr
65                  70                  75                  80

Met Ala Gly Gln Val Tyr Glu Ala Met Gly His Ala Gly Phe Leu Asp
                85                  90                  95

Ser Asn Met Val Val Ile Leu Asn Asp Ser Arg His Thr Leu Leu Pro
            100                 105                 110

Lys Ala Asp Ser Gln Ser Lys Met Ser Ile Asn Ala Leu Ser Ser Ala
        115                 120                 125

Leu Ser Lys Val Gln Ser Ser Lys Gly Phe Arg Lys Phe Arg Glu Ala
    130                 135                 140

Ala Lys Gly Leu Ser Lys Trp Phe Gly Lys Gly Met His Glu Phe Ala
145                 150                 155                 160

Ala Lys Ile Asp Glu Tyr Ala Arg Gly Met Ile Gly Pro His Gly Ala
                165                 170                 175

Thr Leu Phe Glu Glu Leu Gly Xaa Tyr Tyr Ile Gly Pro Ile Asp Gly
            180                 185                 190

Asn Asn Ile Asp Asp Leu Ile Cys Val Leu Lys Glu Val Ser Thr Leu
        195                 200                 205

Asp Ser Thr Gly Pro Val Leu Val His Val Ile Thr Glu Asn Glu Lys
    210                 215                 220

Asp Ser Gly Gly Glu Phe Asn Ser Glu Ile Thr Pro Asp Glu Glu Gly
225                 230                 235                 240

Pro Pro Asp Ser Ser Gln Asp Ile Leu Lys Phe Leu Glu Asn Gly Leu
```

```
                    245                 250                 255
Ser Arg Thr Tyr Asn Asp Cys Phe Val Glu Ser Leu Ile Ala Glu Ala
                260                 265                 270

Glu Asn Asp Lys His Ile Val Val His Gly Gly Met Gly Ile Asp
            275                 280                 285

Arg Ser Ile Gln Leu Phe Gln Ser Arg Phe Pro Asp Arg Phe Phe Asp
        290                 295                 300

Leu Gly Ile Ala Glu Gln His Ala Val Thr Phe Ser Ala Gly Leu Ala
305                 310                 315                 320

Cys Gly Gly Leu Lys Pro Phe Cys Ile Ile Pro Ser Thr Phe Leu Gln
                325                 330                 335

Arg Ala Tyr Asp Gln Ile Val Glu Asp Val Asp Met Gln Lys Ile Pro
            340                 345                 350

Val Arg Phe Ala Ile Thr Ser Ala Gly Leu Val Gly Ser Glu Gly Pro
        355                 360                 365

Thr Asn Ser Gly Pro Phe Asp Ile Thr Phe Met Ser Cys Leu Pro Asn
    370                 375                 380

Met Ile Val Met Ser Pro Ser Asn Glu Asp Glu Leu Ile Asp Met Val
385                 390                 395                 400

Ala Thr Ala Ala Met Val Glu Asp Arg Pro Ile Cys Phe Arg Tyr Pro
                405                 410                 415

Lys Gly Ala Ile Val Gly Thr Ser Gly Thr Leu Ala Tyr Gly Asn Pro
            420                 425                 430

Leu Glu Ile Gly Lys Gly Glu Ile Leu Ala Glu Gly Lys Glu Ile Ala
        435                 440                 445

Phe Leu Gly Tyr Gly Asp Val Val Gln Arg Cys Leu Ile Ala Arg Ser
    450                 455                 460

Leu Leu Phe Asn Phe Gly Ile Gln Ala Thr Val Ala Asn Ala Arg Phe
465                 470                 475                 480

Cys Lys Pro Leu Asp Ile Asp Leu Ile Arg Met Leu Cys Gln Gln His
                485                 490                 495

Asp Phe Leu Ile Thr Val Glu Glu Gly Thr Val Gly Phe Gly Ser
            500                 505                 510

His Val Ser Gln Phe Ile Ser Leu Asp Gly Leu Leu Asp Gly Lys Ile
        515                 520                 525

Lys Trp Arg Pro Ile Val Leu Pro Asp Arg Tyr Ile Glu His Ala Ser
    530                 535                 540

Leu Thr Glu Gln Leu Asp Met Ala Gly Leu Thr Ala His His Ile Ala
545                 550                 555                 560

Ala Thr Ala Leu Thr Leu Leu Gly Arg His Arg Asp Ala Leu Leu Leu
                565                 570                 575

Met Lys

<210> SEQ ID NO 29
<211> LENGTH: 898
<212> TYPE: DNA
<213> ORGANISM: Triticum aestivum
<220> FEATURE:
<221> NAME/KEY: unsure
<222> LOCATION: (145)
<223> OTHER INFORMATION: n = A, C, G or T

<400> SEQUENCE: 29
ccttagagtg ggcttcaatg ggtcctaccc aaacatggta gttatgcccc ctccggacga    60
ggccgagatg ctaaacatgg tggcaaccgc ggcggccatc gacgaccgcc cctcgtgctt   120
```

```
ccgctatccg aggggcaacg gcatnggcgt cccgttgccg gaaaactaca aaggcaccgc    180
catcgaggtc ggcaaaggca ggatcataat cgagggcgag agggtggcgc tgctggggta    240
cgggtcggcg gtgcagtact gcatggccgc ctcgtccatc gtggcgcacc acggcctcag    300
ggtcaccgtc gccgacgcca ggttctgcaa gccgttggac cacgccctca tcaggagcct    360
cgccaagtcc cacgaggtga tcatcaccgt cgaggaaggc tccatcggcg gcttcggttc    420
acacgtggct cagttcatgg ccctggatgg ccttctggac ggcaaactta agtggcggcc    480
ggtggtgctt cccgacaagt acatcgacca tggatcaccg gccgatcagc tggtggaagc    540
cgggctgacg ccgtcgcaca tcgccgcgac ggtgttcaac atcctggggc aggcaagaga    600
ggccctcgcc atcatgacgg tgcagaatgc ctagagccag tgtgctgcct cctatagaga    660
accttgtaca ttttggtcgt taggtgattc agagagatta gtcggcgtca gaaaattaaa    720
tgatcctcat caagggaaac gttggtagtt tttcgttctt tggtgcactg acgttgatgt    780
acatggttaa ttgttcgtgg agtggacaca tacgttgtct ttgtatctgt gaaatgtgta    840
cgtatgttta ttggaaaaaa aaaaaaaaaa aaaaaaaaaa aaaaaaaaaa aaaaaaaa      898
```

<210> SEQ ID NO 30
<211> LENGTH: 210
<212> TYPE: PRT
<213> ORGANISM: Triticum aestivum
<220> FEATURE:
<221> NAME/KEY: UNSURE
<222> LOCATION: (48)
<223> OTHER INFORMATION: Xaa = ANY AMINO ACID

<400> SEQUENCE: 30

```
Leu Arg Val Gly Phe Asn Gly Ser Tyr Pro Asn Met Val Val Met Pro
 1               5                  10                  15

Pro Pro Asp Glu Ala Glu Met Leu Asn Met Val Ala Thr Ala Ala Ala
            20                  25                  30

Ile Asp Asp Arg Pro Ser Cys Phe Arg Tyr Pro Arg Gly Asn Gly Xaa
        35                  40                  45

Gly Val Pro Leu Pro Glu Asn Tyr Lys Gly Thr Ala Ile Glu Val Gly
    50                  55                  60

Lys Gly Arg Ile Ile Ile Glu Gly Glu Arg Val Ala Leu Leu Gly Tyr
65                  70                  75                  80

Gly Ser Ala Val Gln Tyr Cys Met Ala Ala Ser Ser Ile Val Ala His
                85                  90                  95

His Gly Leu Arg Val Thr Val Ala Asp Ala Arg Phe Cys Lys Pro Leu
            100                 105                 110

Asp His Ala Leu Ile Arg Ser Leu Ala Lys Ser His Glu Val Ile Ile
        115                 120                 125

Thr Val Glu Glu Gly Ser Ile Gly Gly Phe Gly Ser His Val Ala Gln
    130                 135                 140

Phe Met Ala Leu Asp Gly Leu Leu Asp Gly Lys Leu Lys Trp Arg Pro
145                 150                 155                 160

Val Val Leu Pro Asp Lys Tyr Ile Asp His Gly Ser Pro Ala Asp Gln
                165                 170                 175

Leu Val Glu Ala Gly Leu Thr Pro Ser His Ile Ala Ala Thr Val Phe
            180                 185                 190

Asn Ile Leu Gly Gln Ala Arg Glu Ala Leu Ala Ile Met Thr Val Gln
        195                 200                 205

Asn Ala
```

-continued

<210> SEQ ID NO 31
<211> LENGTH: 1404
<212> TYPE: DNA
<213> ORGANISM: Triticum aestivum

<400> SEQUENCE: 31

| | | | | | |
|---|---|---|---|---|---|
| ttgcaatctt | gagaaggagg | agaggaaaca | atggcgctct | cgtcgacctt | ctccctcccg | 60 |
| cggggcttcc | tcggcgtgct | gcctcaggag | caccatttcg | ctcccgccgt | cgagctccag | 120 |
| gccaagccgc | tcaagacgcc | gaggaggagg | tcgtccggca | tttctgcgtc | gctgtcggag | 180 |
| agggaagcag | agtaccactc | gcagcggccg | ccgacgccgc | tgctggacac | cgtgaactac | 240 |
| cccatccaca | tgaagaacct | gtccctcaag | gagctgcagc | agctctccga | cgagctgcgc | 300 |
| tccgacgtca | tcttccacgt | ctccaagacc | ggcggccacc | tcgggtccag | cctcggcgtc | 360 |
| gtcgagctca | ccgtcgcgct | gcactacgtc | ttcaacaccc | gcaggacaa | gctcctctgg | 420 |
| gacgtcggcc | accagtcgta | cccgcacaag | attctgacgg | gcggcgcga | taagatgccg | 480 |
| acgatgcggc | agaccaacgg | cctgtccggc | ttcgtcaagc | gctccgagag | cgagtacgac | 540 |
| agcttcggca | ccggccacag | ctccaccacc | atctccgccg | ccctcgggat | ggccgtcggg | 600 |
| agggacctca | agggcgcgaa | gaacaacgtg | gtggcggtga | ttgggacgg | ggccatgacg | 660 |
| gccgggcagg | cgtacgaggc | gatgaacaac | gccggctacc | tcgactcgga | catgatcgtg | 720 |
| atcctcaacg | acaacaagca | ggtgtcgctg | ccgacggcga | cgctcgacgg | gccggcgccg | 780 |
| cccgtgggcg | cgctcagcgg | cgccctcagc | aagctgcagt | ccagccggcc | gctcagggag | 840 |
| ctgagggagg | tggccaaggg | agtgacgaag | caaatcggcg | ggtcggtgca | cgagatcgcg | 900 |
| gccaaggtgg | acgagtacgc | ccgcggcatg | atcagcggct | ccgggtcgtc | gctcttcgag | 960 |
| gagctcgggc | tgtattacat | cggccccgtc | gacggccaca | acattgacga | cctcatcacc | 1020 |
| atccttcggg | aggtcaaggg | caccaagacc | accgggccgg | tgctcatcca | tgtcatcacc | 1080 |
| gagaaaggcc | gcggctaccc | ctacgccgag | cgagcctccg | acaagtacca | acgggtggca | 1140 |
| aagttcgatc | cggcgaccgg | gaggcagttc | aagggtccgg | ccaagacgcc | ttcctacaac | 1200 |
| aactacttcg | cggagccgct | catagcccag | gcggggcaag | acagcaagat | cgtggcattc | 1260 |
| caccccggcca | tgggggcgg | gacggggctc | aactacttcc | tccgccgctt | ccccaaccgg | 1320 |
| ggcttccaag | tcgaatccgc | taaacagaac | gccgtaaccc | ttcccggccg | cctggccggc | 1380 |
| aagggggtta | aacccttctg | cgca | | | | 1404 |

<210> SEQ ID NO 32
<211> LENGTH: 458
<212> TYPE: PRT
<213> ORGANISM: Triticum aestivum

<400> SEQUENCE: 32

Met Ala Leu Ser Ser Thr Phe Ser Leu Pro Arg Gly Phe Leu Gly Val
 1               5                   10                  15

Leu Pro Gln Glu His His Phe Ala Pro Ala Val Glu Leu Gln Ala Lys
             20                  25                  30

Pro Leu Lys Thr Pro Arg Arg Arg Ser Ser Gly Ile Ser Ala Ser Leu
         35                  40                  45

Ser Glu Arg Glu Ala Glu Tyr His Ser Gln Arg Pro Pro Thr Pro Leu
     50                  55                  60

Leu Asp Thr Val Asn Tyr Pro Ile His Met Lys Asn Leu Ser Leu Lys
 65                  70                  75                  80

```
Glu Leu Gln Gln Leu Ser Asp Glu Leu Arg Ser Asp Val Ile Phe His
             85                  90                  95

Val Ser Lys Thr Gly His Leu Gly Ser Ser Leu Gly Val Val Glu
            100                 105                 110

Leu Thr Val Ala Leu His Tyr Val Phe Asn Thr Pro Gln Asp Lys Leu
            115                 120                 125

Leu Trp Asp Val Gly His Gln Ser Tyr Pro His Lys Ile Leu Thr Gly
130                 135                 140

Arg Arg Asp Lys Met Pro Thr Met Arg Gln Thr Asn Gly Leu Ser Gly
145                 150                 155                 160

Phe Val Lys Arg Ser Glu Ser Glu Tyr Asp Ser Phe Gly Thr Gly His
                165                 170                 175

Ser Ser Thr Thr Ile Ser Ala Ala Leu Gly Met Ala Val Gly Arg Asp
            180                 185                 190

Leu Lys Gly Ala Lys Asn Asn Val Val Ala Val Ile Gly Asp Gly Ala
            195                 200                 205

Met Thr Ala Gly Gln Ala Tyr Glu Ala Met Asn Asn Ala Gly Tyr Leu
210                 215                 220

Asp Ser Asp Met Ile Val Ile Leu Asn Asp Asn Lys Gln Val Ser Leu
225                 230                 235                 240

Pro Thr Ala Thr Leu Asp Gly Pro Ala Pro Val Gly Ala Leu Ser
                245                 250                 255

Gly Ala Leu Ser Lys Leu Gln Ser Ser Arg Pro Leu Arg Glu Leu Arg
            260                 265                 270

Glu Val Ala Lys Gly Val Thr Lys Gln Ile Gly Gly Ser Val His Glu
            275                 280                 285

Ile Ala Ala Lys Val Asp Glu Tyr Ala Arg Gly Met Ile Ser Gly Ser
290                 295                 300

Gly Ser Ser Leu Phe Glu Glu Leu Gly Leu Tyr Tyr Ile Gly Pro Val
305                 310                 315                 320

Asp Gly His Asn Ile Asp Asp Leu Ile Thr Ile Leu Arg Glu Val Lys
                325                 330                 335

Gly Thr Lys Thr Thr Gly Pro Val Leu Ile His Val Ile Thr Glu Lys
            340                 345                 350

Gly Arg Gly Tyr Pro Tyr Ala Glu Arg Ala Ser Asp Lys Tyr Gln Arg
            355                 360                 365

Val Ala Lys Phe Asp Pro Ala Thr Gly Arg Gln Phe Lys Gly Pro Ala
370                 375                 380

Lys Thr Pro Ser Tyr Asn Asn Tyr Phe Ala Glu Pro Leu Ile Ala Gln
385                 390                 395                 400

Ala Gly Gln Asp Ser Lys Ile Val Ala Phe His Pro Ala Met Gly Gly
                405                 410                 415

Gly Thr Gly Leu Asn Tyr Phe Leu Arg Arg Phe Pro Asn Arg Gly Phe
            420                 425                 430

Gln Val Glu Ser Ala Lys Gln Asn Ala Val Thr Leu Pro Gly Arg Leu
            435                 440                 445

Ala Gly Lys Gly Val Lys Pro Phe Cys Ala
450                 455

<210> SEQ ID NO 33
<211> LENGTH: 719
<212> TYPE: PRT
<213> ORGANISM: Capsicum annuum
```

<400> SEQUENCE: 33

```
Met Ala Leu Cys Ala Tyr Ala Phe Pro Gly Ile Leu Asn Arg Thr Val
  1               5                  10                  15

Ala Val Ala Ser Asp Ala Ser Lys Pro Thr Pro Leu Phe Ser Glu Trp
             20                  25                  30

Ile His Gly Thr Asp Leu Gln Phe Gln Phe His Gln Lys Leu Thr Gln
         35                  40                  45

Val Lys Lys Arg Ser Arg Thr Val Gln Ala Ser Leu Ser Glu Ser Gly
     50                  55                  60

Glu Tyr Tyr Thr Gln Arg Pro Pro Thr Pro Ile Val Asp Thr Ile Asn
 65                  70                  75                  80

Tyr Pro Ile His Met Lys Asn Leu Ser Leu Lys Glu Leu Lys Gln Leu
                 85                  90                  95

Ala Asp Glu Leu Arg Ser Asp Thr Ile Phe Asn Val Ser Lys Thr Gly
             100                 105                 110

Gly His Leu Gly Ser Ser Leu Gly Val Val Glu Leu Thr Val Ala Leu
         115                 120                 125

His Tyr Val Phe Asn Ala Pro Gln Asp Arg Ile Leu Trp Asp Val Gly
130                 135                 140

His Gln Ser Tyr Pro His Lys Ile Leu Thr Gly Arg Arg Glu Lys Met
145                 150                 155                 160

Ser Thr Leu Arg Gln Thr Asn Gly Leu Ala Gly Phe Thr Lys Arg Ser
                165                 170                 175

Glu Ser Glu Tyr Asp Cys Phe Gly Thr Gly His Ser Ser Thr Thr Ile
            180                 185                 190

Ser Ala Gly Leu Gly Met Ala Val Gly Arg Asp Leu Lys Gly Arg Asn
        195                 200                 205

Asn Asn Val Ile Ala Val Ile Gly Asp Gly Ala Met Thr Ala Gly Gln
    210                 215                 220

Ala Tyr Glu Ala Met Asn Asn Ala Gly Tyr Leu Asp Ser Asp Met Ile
225                 230                 235                 240

Val Ile Leu Asn Asp Asn Arg Gln Val Ser Leu Pro Thr Ala Thr Leu
                245                 250                 255

Asp Gly Pro Val Pro Pro Val Gly Ala Leu Ser Ser Ala Leu Ser Arg
            260                 265                 270

Leu Gln Ser Asn Arg Pro Leu Arg Glu Leu Arg Glu Val Ala Lys Gly
        275                 280                 285

Val Thr Lys Gln Ile Gly Gly Pro Met His Glu Leu Ala Ala Lys Val
    290                 295                 300

Asp Glu Tyr Ala Arg Gly Met Ile Ser Gly Ser Gly Ser Thr Leu Phe
305                 310                 315                 320

Glu Glu Leu Gly Leu Tyr Tyr Ile Gly Pro Val Asp Gly His Asn Ile
                325                 330                 335

Asp Asp Leu Ile Ser Ile Leu Lys Glu Val Arg Ser Thr Lys Thr Thr
            340                 345                 350

Gly Pro Val Leu Ile His Val Val Thr Glu Lys Gly Arg Gly Tyr Pro
        355                 360                 365

Tyr Ala Glu Arg Ala Ala Asp Lys Tyr His Gly Val Ala Lys Phe Asp
    370                 375                 380

Pro Ala Thr Gly Lys Gln Phe Lys Gly Ser Ala Lys Thr Gln Ser Tyr
385                 390                 395                 400

Thr Thr Tyr Phe Ala Glu Ala Leu Ile Ala Glu Ala Glu Ala Asp Lys
                405                 410                 415
```

-continued

```
Asp Ile Val Ala Ile His Ala Ala Met Gly Gly Gly Thr Gly Met Asn
            420                 425                 430

Leu Phe Leu Arg Arg Phe Pro Thr Arg Cys Phe Asp Val Gly Ile Ala
            435                 440                 445

Glu Gln His Ala Val Thr Phe Ala Ala Gly Leu Ala Cys Glu Gly Leu
            450                 455                 460

Lys Pro Phe Cys Ala Ile Tyr Ser Ser Phe Met Gln Arg Ala Tyr Asp
465                 470                 475                 480

Gln Val Val His Asp Val Asp Leu Gln Lys Leu Pro Val Arg Phe Ala
                485                 490                 495

Met Asp Arg Ala Gly Leu Val Gly Ala Asp Gly Pro Thr His Cys Gly
            500                 505                 510

Ala Phe Asp Val Thr Phe Met Ala Cys Leu Pro Asn Met Val Val Met
            515                 520                 525

Ala Pro Ser Asp Glu Ala Glu Leu Phe His Ile Val Ala Thr Ala Ala
            530                 535                 540

Ala Ile Asp Asp Arg Pro Ser Cys Phe Arg Tyr Pro Arg Gly Asn Gly
545                 550                 555                 560

Ile Gly Val Glu Leu Pro Ala Gly Asn Lys Gly Ile Pro Leu Glu Val
                565                 570                 575

Gly Lys Gly Arg Ile Leu Val Glu Gly Glu Arg Val Ala Leu Leu Gly
            580                 585                 590

Tyr Gly Ser Ala Val Gln Asn Cys Leu Ala Ala Ser Val Leu Glu
            595                 600                 605

Ser Arg Gly Leu Gln Val Thr Val Ala Asp Ala Arg Phe Cys Lys Pro
            610                 615                 620

Leu Asp Arg Ala Leu Ile Arg Ser Leu Ala Lys Ser His Glu Val Leu
625                 630                 635                 640

Val Thr Val Glu Lys Gly Ser Ile Gly Gly Phe Gly Ser His Val Val
                645                 650                 655

Gln Phe Met Ala Leu Asp Gly Leu Leu Asp Gly Lys Leu Lys Trp Arg
            660                 665                 670

Pro Ile Val Leu Pro Asp Arg Tyr Ile Asp His Gly Ser Pro Ala Asp
            675                 680                 685

Gln Leu Ala Glu Ala Gly Leu Thr Pro Ser His Ile Ala Ala Thr Val
            690                 695                 700

Phe Asn Ile Leu Gly Gln Thr Arg Glu Ala Leu Glu Val Met Thr
705                 710                 715

<210> SEQ ID NO 34
<211> LENGTH: 594
<212> TYPE: PRT
<213> ORGANISM: Oryza sativa

<400> SEQUENCE: 34

Asn Tyr Pro Ile His Met Lys Asn Leu Ser Leu Lys Glu Leu Gln Gln
 1               5                  10                  15

Leu Ala Asp Glu Leu Arg Ser Asp Val Ile Phe His Val Ser Lys Thr
            20                  25                  30

Gly Gly His Leu Gly Ser Ser Leu Gly Val Val Glu Leu Thr Val Ala
            35                  40                  45

Leu His Tyr Val Phe Asn Thr Pro Gln Asp Lys Ile Leu Trp Asp Val
        50                  55                  60

Gly His Gln Ser Tyr Pro His Lys Ile Leu Thr Gly Arg Arg Asp Lys
```

-continued

```
             65                  70                  75                  80
Met Pro Thr Met Arg Gln Thr Asn Gly Leu Ser Gly Phe Thr Lys Arg
                     85                  90                  95

Ser Glu Ser Glu Tyr Asp Ser Phe Gly Thr Gly His Ser Ser Thr Thr
                    100                 105                 110

Ile Ser Ala Ala Leu Gly Met Ala Val Gly Arg Asp Leu Lys Gly Gly
                    115                 120                 125

Lys Asn Asn Val Val Ala Val Ile Gly Asp Gly Ala Met Thr Ala Gly
                    130                 135                 140

Gln Ala Tyr Glu Ala Met Asn Asn Ala Gly Tyr Leu Asp Ser Asp Met
145                 150                 155                 160

Ile Val Ile Leu Asn Asp Asn Lys Gln Val Ser Leu Pro Thr Ala Thr
                    165                 170                 175

Leu Asp Gly Pro Ala Pro Pro Val Gly Ala Leu Ser Ser Ala Leu Ser
                    180                 185                 190

Lys Leu Gln Ser Ser Arg Pro Leu Arg Glu Leu Arg Glu Val Ala Lys
                    195                 200                 205

Gly Val Thr Lys Gln Ile Gly Gly Ser Val His Glu Leu Ala Ala Lys
                    210                 215                 220

Val Asp Glu Tyr Ala Arg Gly Met Ile Ser Gly Ser Gly Ser Thr Leu
225                 230                 235                 240

Phe Glu Glu Leu Gly Leu Tyr Tyr Ile Gly Pro Val Asp Gly His Asn
                    245                 250                 255

Ile Asp Asp Leu Ile Thr Ile Leu Arg Glu Val Lys Ser Thr Lys Thr
                    260                 265                 270

Thr Gly Pro Val Leu Ile His Val Val Thr Glu Lys Gly Arg Gly Tyr
                    275                 280                 285

Pro Tyr Ala Glu Arg Ala Ala Asp Lys Tyr His Gly Val Ala Lys Phe
                    290                 295                 300

Asp Pro Ala Thr Gly Lys Gln Phe Lys Ser Pro Ala Lys Thr Leu Ser
305                 310                 315                 320

Tyr Thr Asn Tyr Phe Ala Glu Ala Leu Ile Ala Glu Ala Glu Gln Asp
                    325                 330                 335

Asn Arg Val Val Ala Ile His Ala Ala Met Gly Gly Gly Thr Gly Leu
                    340                 345                 350

Asn Tyr Phe Leu Arg Arg Phe Pro Asn Arg Cys Phe Asp Val Gly Ile
                    355                 360                 365

Ala Glu Gln His Ala Val Thr Phe Ala Ala Gly Leu Ala Cys Glu Gly
                    370                 375                 380

Leu Lys Pro Phe Cys Ala Ile Tyr Ser Ser Phe Leu Gln Arg Gly Tyr
385                 390                 395                 400

Asp Gln Val Val His Asp Val Asp Leu Gln Lys Leu Pro Val Arg Phe
                    405                 410                 415

Ala Met Asp Arg Ala Gly Leu Val Gly Ala Asp Gly Pro Thr His Cys
                    420                 425                 430

Gly Ala Phe Asp Val Thr Tyr Met Ala Cys Leu Pro Asn Met Val Val
                    435                 440                 445

Met Ala Pro Ser Asp Glu Ala Glu Leu Cys His Met Val Ala Thr Ala
                    450                 455                 460

Ala Ala Ile Asp Asp Arg Pro Ser Cys Phe Arg Tyr Pro Arg Gly Asn
465                 470                 475                 480

Gly Ile Gly Val Pro Leu Pro Pro Asn Tyr Lys Gly Val Pro Leu Glu
                    485                 490                 495
```

-continued

```
Val Gly Lys Gly Arg Val Leu Leu Glu Gly Glu Arg Val Ala Leu Leu
            500                 505                 510

Gly Tyr Gly Ser Ala Val Gln Tyr Cys Leu Ala Ala Ser Leu Val
        515                 520                 525

Glu Arg His Gly Leu Lys Val Thr Val Ala Asp Ala Arg Phe Cys Lys
        530                 535                 540

Pro Leu Asp Gln Thr Leu Ile Arg Arg Leu Ala Ser Ser His Glu Val
545                 550                 555                 560

Leu Leu Thr Val Glu Glu Gly Ser Ile Gly Gly Phe Gly Ser His Val
                565                 570                 575

Ala Gln Phe Met Ala Leu Asp Gly Leu Leu Asp Gly Lys Leu Lys Trp
                580                 585                 590

Arg Pro
```

US 7,195,887 B2

RICE 1-DEOXY-D-XYLULOSE 5-PHOSPHATE SYNTHASE AND DNA ENCODING THEREOF

This application is a divisional of U.S. application Ser. No. 10/427,590, filed Apr. 30, 2003, now U.S. Pat. No. 7,132,250, which is a divisional of U.S. application Ser. No. 09/857,556, filed Jun. 4, 2001, issued as U.S. Pat. No. 6,558,915, the entire contents of which are herein incorporated by reference, which is the National Stage Application, according to 35 U.S.C. 371, of International Application No. PCT/US99/28587, filed Dec. 2, 1999, which claims the benefit of U.S. Provisional Application No. 60/110,779, filed Dec. 3, 1998.

FIELD OF THE INVENTION

This invention is in the field of plant molecular biology. More specifically, this invention pertains to nucleic acid fragments encoding 1-deoxy-D-xylulose 5-phosphate synthase in plants and seeds.

BACKGROUND OF THE INVENTION

Isoprenoids comprise the largest family of natural products, including numerous secondary compounds, which play different functional roles in plants such as hormones, photosynthetic pigments, electron carriers, and structural components of membranes. The fundamental unit in isoprenoid biosynthesis, isopentenyl diphosphate (IPP), is normally synthesized by the condensation of acetyl CoA through the mevalonate pathway. In many organisms including several bacteria, algae and plant plastids, IPP is synthesized by a mevalonate-independent pathway. The initial step in this pathway is the condensation of pyruvate and glyceraldehyde 3-phosphate to form 1-deoxy-D-xylulose 4-phosphate which behaves as the precursor for IPP, thiamine (vitamin B1), or pyridoxine (vitamin B2). This initial step is catalyzed by 1-deoxy-D-xylulose 5-phosphate synthase (DXPS), a member of a distinct protein family. In *E. coli* DXPS shows sequence similarity to both transketolases and the E1 subunit of pyruvate dehydrogenase (Sprenger (1997) *Proc. Natl. Acad. Sci. USA* 94:12857–12862).

SUMMARY OF THE INVENTION

The present invention relates to isolated polynucleotides comprising a nucleotide sequence encoding a first polypeptide of at least 170 amino acids that has at least 95% identity based on the Clustal method of alignment when compared to a polypeptide selected from the group consisting of a corn 1-deoxy-D-xylulose 5-phosphate synthase polypeptide of SEQ ID NOs:2, 4, 18. 20, 22, and 24, a rice 1-deoxy-D-xylulose 5-phosphate synthase polypeptide of SEQ ID NOs: 6, 8, 26, and 28, a soybean 1-deoxy-D-xylulose 5-phosphate synthase polypeptide of SEQ ID NOs:10 and 12, a wheat 1-deoxy-D-xylulose 5-phosphate synthase polypeptide of SEQ ID NO:14, 16, 30, and 32. The present invention also relates to an isolated polynucleotide comprising the complement of the nucleotide sequences described above.

It is preferred that the isolated polynucleotide of the claimed invention consists of a nucleic acid sequence selected from the group consisting of SEQ ID NOs:1, 3, 5, 7, 9, 11, 13, 15, 17, 19, 21, 23, 25, 27, 29, and 31 that codes for the polypeptide selected from the group consisting of SEQ ID NOs:2, 4, 6, 8, 10, 12, 14, 16, 18, 20, 22, 24, 26, 28, 30, and 32. The present invention also relates to an isolated polynucleotide comprising a nucleotide sequences of at least one of 40 (preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a 1-deoxy-D-xylulose 5-phosphate synthase polypeptide of at least 170 amino acids comprising at least 95% homology based on the Clustal method of alignment compared to a polypeptide selected from the group consisting of SEQ ID NOs:2, 4, 6, 8, 10, 12, 14, 16, 18, 20, 22, 24, 26, 28, 30, and 32.

The present invention relates to a method of selecting an isolated polynucleotide that affects the level of expression of a 1-deoxy-D-xylulose 5-phosphate synthase polypeptide in a host cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a 1-deoxy-D-xylulose 5-phosphate synthase polypeptide in the host cell containing the isolated polynucleotide; and (d) comparing the level of a 1-deoxy-D-xylulose 5-phosphate synthase polypeptide in the host cell containing the isolated polynucleotide with the level of a 1-deoxy-D-xylulose 5-phosphate synthase polypeptide in a host cell that does not contain the isolated polynucleotide.

The present invention relates to a method of obtaining a nucleic acid fragment encoding a substantial portion of a 1-deoxy-D-xylulose 5-phosphate synthase polypeptide gene, preferably a plant 1-deoxy-D-xylulose 5-phosphate synthase polypeptide gene, comprising the steps of: synthesizing an oligonucleotide primer comprising a nucleotide sequence of at least one of 40 (preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, and the complement of such nucleotide sequences; and amplifying a nucleic acid fragment (preferably a cDNA inserted in a cloning vector) using the oligonucleotide primer. The amplified nucleic acid fragment preferably will encode a portion of a 1-deoxy-D-xylulose 5-phosphate synthase amino acid sequence.

The present invention also relates to a method of obtaining a nucleic acid fragment encoding all or a substantial portion of the amino acid sequence encoding a 1-deoxy-D-xylulose 5-phosphate synthase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a 1-deoxy-D-xylulose 5-phosphate synthase, the method comprising the steps of: (a) transforming a host cell with a chimeric gene comprising a nucleic acid fragment encoding a 1-deoxy-D-xylulose 5-phosphate synthase, operably linked to suitable regulatory sequences; (b) growing the transformed host cell under conditions that are suitable for expression of the chimeric gene wherein expression of the chimeric gene results in production of 1-deoxy-D-xylulose 5-phosphate synthase in the transformed host cell; (c) optionally purifying the 1-deoxy-D-xylulose 5-phosphate synthase expressed by the transformed host cell; (d) treating the 1-deoxy-D-xylulose 5-phosphate synthase with a compound to be tested; and (e) comparing the activity of the 1-deoxy-D-xylulose 5-phosphate synthase that has been treated with a test compound to the activity of an untreated 1-deoxy-D-xylulose 5-phosphate synthase, thereby selecting compounds with potential for inhibitory activity.

BRIEF DESCRIPTION OF THE DRAWING AND SEQUENCE DESCRIPTIONS

The invention can be more fully understood from the following detailed description and the accompanying drawing and Sequence Listing which form a part of this application.

FIGS. 1A–1D a comparison of the amino acid sequences of the 1-deoxy-D-xylulose 5-phosphate synthase from soybean clone sdp2c.pk001.h19 (SEQ ID NO:10), soybean clone sgc1c.pk001.c11 (SEQ ID NO:12), rice clone r10n.pk081.m14 (SEQ ID NO:26), *Capsicum annuum* set forth in NCBI General Identifier No. 3559816 (SEQ ID NO:33), and *Oryza sativa* set forth in NCBI General Identifier No. 3913239 (SEQ ID NO:34). Amino acids conserved among all sequences are indicated with an asterisk (*) on the top row; dashes are used by the program to maximize alignment of the sequences.

Table 1 lists the polypeptides that are described herein the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Isopentenyl Diphosphate Biosynthetic Enzymes

| Protein | Clone Designation | SEQ ID NO: (Nucleotide) | SEQ ID NO: (Amino Acid) |
| --- | --- | --- | --- |
| Corn 1-Deoxy-D-Xylulose 5-Phosphate Synthase | Contig of: csi1n.pk0040.e11 csi1n.pk0043.b2 cen5.pk0058.b3 p0014.ctuse54r | 1 | 2 |
| Corn 1-Deoxy-D-Xylulose 5-Phosphate Synthase | p0006.cbyvq72r | 3 | 4 |
| Rice 1-Deoxy-D-Xylulose 5-Phosphate Synthase | Contig of: r10n.pk081.m14 rlr24.pk0087.h4 | 5 | 6 |

TABLE 1-continued

Isopentenyl Diphosphate Biosynthetic Enzymes

| Protein | Clone Designation | SEQ ID NO: (Nucleotide) | SEQ ID NO: (Amino Acid) |
| --- | --- | --- | --- |
| Rice 1-Deoxy-D-Xylulose 5-Phosphate Synthase | rr1.pk089.l13 | 7 | 8 |
| Soybean 1-Deoxy-D-Xylulose 5-Phosphate Synthase | sdp2c.pk001.h19 | 9 | 10 |
| Soybean 1-Deoxy-D-Xylulose 5-Phosphate Synthase | sgc1c.pk001.c11 | 11 | 12 |
| Wheat 1-Deoxy-D-Xylulose 5-Phosphate Synthase | wlm4.pk0022.h2 | 13 | 14 |
| Wheat 1-Deoxy-D-Xylulose 5-Phosphate Synthase | wlm4.pk0009.c9 | 15 | 16 |
| Corn 1-Deoxy-D-Xylulose 5-Phosphate Synthase | Contig of: cen5.pk0058.b3: fis csi1n.pk0040.e11 | 17 | 18 |
| Corn 1-Deoxy-D-Xylulose 5-Phosphate Synthase | p0006.cbyvq72r: fis | 19 | 20 |
| Corn 1-Deoxy-D-Xylulose 5-Phosphate Synthase | p0031.ccmcg27ra | 21 | 22 |
| Corn 1-Deoxy-D-Xylulose 5-Phosphate Synthase | p0126.cnlcx46r | 23 | 24 |
| Rice 1-Deoxy-D-Xylulose 5-Phosphate Synthase | r10n.pk081.m14: fis | 25 | 26 |
| Rice 1-Deoxy-D-Xylulose 5-Phosphate Synthase | rr1.pk089.l13: fis | 27 | 28 |
| Wheat 1-Deoxy-D-Xylulose 5-Phosphate Synthase | wlm4.pk0009.c9 | 29 | 30 |
| Wheat 1-Deoxy-D-Xylulose 5-Phosphate Synthase | wlm4.pk0022.h2 | 31 | 32 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs:1, 3, 5, 7, 9, 11, 13, 15, 17, 19, 21, 23, 25, 27, 29, 31 and the complement of such sequences.

As used herein. "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31 and the complement of such nucleotide sequences may be used in methods of selecting an isolated polynucleotide that affects the expression of a polypeptide in a plant cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide. Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several 1-deoxy-D-xylulose 5-phosphate synthases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other 1-deoxy-D-xylulose 5-phosphate synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follows the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as 1-deoxy-D-xylulose 5-phosphate synthase) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29. 31, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Inmunol.* 36:1–34; Maniatis).

The nucleic acid fragments of the instant invention may be used to create transgenic plants in which the disclosed polypeptide is present at higher or lower levels than normal or in cell types or developmental stages in which it is not normally found. This would have the effect of altering the level of isopentenyl diphosphate in those cells. Manipulation of this gene in the endosperm of plants could result in increased xanthophyll levels, which has value as coloring agents in poultry feeds. In *Arabidopsis*, mutants in this gene are carotenoid deficient and albino. Because this mevalonate-independent pathway appears to be unique to microorganisms and plastids inhibitors of this enzyme should have no affect on animals. Overexpression of this gene will produce the active enzyme for high-through screening to find inhibitors for this enzyme. These inhibitors may lead to discover a novel herbicide.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the chimeric gene described above may be further supplemented by altering the coding sequence to encode the instant polypeptide with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or-cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptide (or portions thereof) may be produced in heterologous host cells, particularly in the cells of microbial hosts, and can be used to prepare antibodies to the these proteins by methods well known to those skilled in the art. The antibodies are useful for detecting the polypeptide of the instant invention in situ in cells or in vitro in cell extracts. Preferred heterologous host cells for production of the instant polypeptide are microbial hosts. Microbial expression systems and expression vectors containing regulatory sequences that direct high level expression of foreign proteins are well known to those skilled in the art. Any of these could be used to construct a chimeric gene for production of the instant polypeptide. This chimeric gene could then be introduced into appropriate microorganisms via transformation to provide high level expression of the encoded 1-deoxy-D-xylulose 5-phosphate synthase. An example of a vector for high level expression of the instant polypeptide in a bacterial host is provided (Example 6).

Additionally, the instant polypeptide can be used as a target to facilitate design and/or identification of inhibitors of those enzymes that may be useful as herbicides. This is desirable because the polypeptide described herein catalyzes isopentenyl diphosphate synthesis via the mevalonate-independent pathway. Accordingly, inhibition of the activity of the enzyme described herein could lead to inhibition of plant growth. Thus, the instant 1-deoxy-D-xylulose 5-phosphate synthase could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080). nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cen5 | Corn Endosperm 30 Days After Pollination | cen5.pk0058.b3 |
| csi1n | Corn Silk* | csi1n.pk0040.e11 |
| csi1n | Corn Silk* | csi1n.pk0043.b2 |
| p0006 | Corn, Young Shoot | p0006.cbyvq72r |
| p0014 | Corn Leaves 7 and 8 from Plant Transformed with uaz151 (G-protein) Gene, *C. heterostrophus* Resistant | p0014.ctuse54r |
| p0031 | Corn Shoot Culture | p0031.ccmcg27ra |
| p0126 | Corn Leaf Tissue Pooled From V8–V10 Stages**, Night-Harvested | p0126.cnlcx46r |
| rl0n | Rice 15 Day Old Leaf* | rl0n.pk081.m14 |
| rlr24 | Rice Leaf 15 Days After Germination, 24 Hours After Infection of Strain *Magaporthe grisea* 4360-R-62 (AVR2-YAMO); Resistant | rlr24.pk0087.h4 |
| rr1 | Rice Root of Two Week Old Developing Seedling | rr1.pk089.l13 |
| sdp2c | Soybean Developing Pods (6–7 mm) | sdp2c.pk001.h19 |
| sgc1c | Soybean Cotyledon 7 Days After Germination (Young Green) | sgc1c.pk001.c11 |
| wlm4 | Wheat Seedlings 4 Hours After Inoculation With *Erysiphe graminis* f. sp *tritici* | wlm4.pk0009.c9 |
| wlm4 | Wheat Seedlings 4 Hours After Inoculation With *Erysiphe graminis* f. sp *tritici* | wlm4.pk0022.h2 |

*These libraries were normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding 1-deoxy-D-xylulose 5-phosphate synthases were identified by conducting BLAST (Basic Local Alignment Search Tool; Altschul et al. (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding 1-Deoxy-D-Xylulose 5-Phosphate Synthase The BLASTX search using the nucleotide sequences from clones listed in Table 3 revealed similarity of the polypeptides encoded by the cDNAs to 1-deoxy-D-xylulose 5-phosphate synthase from *Capsicum annuum* (NCBI General Identifier No. 3559816). Shown in Table 3 are the BLAST results for individual ESTs ("EST"), contigs assembled from two or more ESTs ("Contig"), or sequences encoding the entire protein derived from the entire cDNA inserts comprising the indicated cDNA clones (FIS), a contig, or an FIS and PCR ("CGS"):

TABLE 3

BLAST Results for Sequences Encoding Polypeptides Homologous to 1-Deoxy-D-Xylulose 5-Phosphate Synthase

| Clone | Status | BLAST pLog Score 3559816 |
| --- | --- | --- |
| Contig of: | Contig | 84.70 |
| csi1n.pk0040.e11 | | |
| csi1n.pk0043.b2 | | |
| cen5.pk0058.b3 | | |
| p0014.ctuse54r | | |
| p0006.cbyvq72r | EST | 66.40 |
| Contig of: | Contig | 18.00 |
| rl0n.pk081.m14 | | |
| rlr24.pk0087.h4 | | |
| rr1.pk089.l13 | EST | 25.30 |
| sdp2c.pk001.h19 | CGS | >254 |
| sgc1c.pk001.c11 | CGS | >254 |
| wlm4.pk0022.h2 | EST | 16.00 |
| wlm4.pk0009.c9 | EST | 62.00 |

Further sequencing of some of the above clones yielded new information. The BLASTX search using the nucleotide sequences from clones listed in Table 4 revealed similarity of the polypeptides encoded by the cDNAs to transketolase 2 from *Oryza sativa* and *Capsicum annuum* (NCBI General Identifier Nos. 5803266 and 3559816, respectively), and 1-deoxy-D-xylulose 5-phosphate synthase from *Oryza sativa, Lycopersicon esculentum*, and *Catharanthus roseus* (NCBI General Identifier Nos. 3913239, 5059160, and 3724087, respectively). Shown in Table 4 are the BLAST results for individual ESTs ("EST"), the sequences of the entire cDNA inserts comprising the indicated cDNA clones ("FIS"), contigs assembled from an FIS and an EST ("Contig*"), or sequences encoding the entire protein derived from an FIS, or an FIS and PCR ("CGS"):

TABLE 4

BLAST Results for Sequences Encoding Polypeptides Homologous to 1-Deoxy-D-Xylulose 5-Phosphate Synthase

| Clone | Status | NCBI General Identifier No. | BLAST pLog Score |
| --- | --- | --- | --- |
| Contig of: cen5.pk0058.b3: fis csi1n.pk0040.e11 | Contig* | 5803266 | 140.00 |
| p0006.cbyvq72r: fis | FIS | 5059160 | >254.00 |
| p0031.ccmcg27ra | EST | 3724087 | 68.52 |
| p0126.cnlcx46r | EST | 5803266 | 32.05 |
| rl0n.pk081.m14: fis | FIS | 3913239 | >254.00 |
| rr1.pk089.l13: fis | CGS | 3559816 | >254.00 |
| wlm4.pk0009.c9 | EST | 3559816 | 91.52 |
| wlm4.pk0022.h2 | Contig | 3913239 | >254.00 |

FIGS. 1A–1D present an alignment of the amino acid sequences set forth in SEQ ID Nos:10, 12 and 26 and the *Capsicum annuum* and *Oryza sativa* sequences (SEQ ID NO:33 and SEQ ID NO:34, respectively). The data in Table 5 represents a calculation of the percent identity of the amino acid sequences set forth in SEQ ID NOs:2, 4. 6, 8, 10, 12, 14, 16, 18, 20, 22, 24, 26, 28, 30, and 32 and the *Capsicum annuum* sequence (SEQ ID NO:33).

TABLE 5

Percent Identity of Amino Acid Sequences Deduced From the Nucleotide Sequences of cDNA Clones Encoding Polypeptides Homologous to 1-Deoxy-D-Xylulose 5-Phosphate Synthase

| SEQ ID NO. | Percent Identity to 3559816 |
| --- | --- |
| 2 | 61.6 |
| 4 | 86.3 |
| 6 | 37.6 |
| 8 | 66.7 |
| 10 | 87.2 |
| 12 | 86.6 |
| 14 | 38.7 |
| 16 | 80.6 |
| 18 | 60.7 |
| 20 | 86.9 |
| 22 | 62.7 |
| 24 | 45.7 |
| 26 | 82.5 |
| 28 | 55.9 |
| 30* | 77.6 |
| 32* | 75.1 |

*SEQ ID NO: 30 encodes the C-terminal fourth of a wheat 1-deoxy-D-xylulose 5-phosphate synthase while SEQ ID NO: 32 encodes the N-terminal third of the protein Sequence alignments and percent identity calculations were performed using the Megalign program of the LASER- GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of corn, rice, and wheat and entire soybean and rice 1-deoxy-D-xylulose 5-phosphate synthases. There are at least two independent 1-deoxy-D-xylulose 5-phosphate synthase variants in each crop. These sequences represent the first corn, soybean, and wheat sequences encoding 1-deoxy-D-xylulose 5-phosphate synthase and variants of rice 1-deoxy-D-xylulose 5-phosphate synthase.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens.*

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at. 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the 0 subunit of the seed storage protein phaseolin from the bean *Phaseolus vulgaris* (Doyle et al. (1986) *J. Biol. Chem.* 261:9228–9238) can be used for expression of the instant polypeptide in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. 1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptide can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Isopentenyl Diphosphate Biosynthetic Enzymes The polypeptide described herein may be produced using any number of methods known to those skilled in the art. Such methods include, but are not limited to, expression in bacteria as described in Example 6. or expression in eukaryotic cell culture, inplanta, and using viral expression systems in suitably infected organisms or cell lines. The instant polypeptide may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptide, if desired, may utilize any number of separation technologies familiar to those skilled in the art of protein purification. Examples of such methods include, but are not limited to, homogenization, filtration, centrifugation, heat denaturation, ammonium sulfate, precipitation, desalting, pH precipitation, ion exchange chromatography, hydrophobic interaction chromatography and affinity chromatography, wherein the affinity ligand represents a substrate, substrate analog or inhibitor. When the instant polypeptide are expressed as fusion proteins, the purification protocol may include the use of an affinity resin which is specific for the fusion protein tag attached to the expressed enzyme or an affinity resin containing ligands which are specific for the enzyme. For example, the instant polypeptide may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptide disclosed herein. Assays may be conducted under well known experimental conditions which permit optimal enzymatic activity. For example, assays for 1-deoxy-D-xylulose 5-phosphate synthase are presented by Sprenger et al. (1998) *Proc. Natl. Acad. Sci. USA* 95:2105–2110).

What is claimed is:

1. An isolated polynucleotide comprising:
   (a) a nucleotide sequence that encodes a polypeptide having 1-deoxy-D-xylulose 5-phosphate synthase activity, wherein the polypeptide has an amino acid sequence of at least 95% sequence identity when compared to SEQ ID NO:26, based on the Clustal method of alignment with pairwise alignment default parameters of KTUPLE=1, GAP PENALTY=3, WINDOW=5 and DIAGONALS SAVED=5, or
   (b) a complement of the nucleotide sequence of (a), wherein the complement and the nucleotide sequence of (a) consist of the same number of nucleotides and are 100% complementary.

2. The polynucleotide of claim 1 wherein the amino acid sequence of the polypeptide comprises SEQ ID NO:26.

3. The polynucleotide of claim 1, wherein the nucleotide sequence of the polynucleotide comprises SEQ ID NO:25.

4. A cell or a virus comprising the polynucleotide of claim 1, wherein the cell is selected from the group consisting of a yeast cell, a bacterial cell, and a plant cell.

5. A method for transforming a cell comprising introducing into a cell the polynucleotide of claim 1.

6. A method for producing a transgenic plant comprising:
   (a) transforming a plant cell with the polynucleotide of claim 1; and
   (b) regenerating a transgenic plant from the transformed plant cell of (a).

7. A recombinant DNA construct comprising the polynucleotide of claim 1 operably linked to at least one regulatory sequence.

8. The recombinant DNA construct of claim 7, wherein the recombinant DNA construct Is an expression vector.

9. A method for altering the level of 1-deoxy-D-xylulose 5-phosphate synthase polypeptide expression in a host cell, the method comprising:
   (a) transforming a host cell with the recombinant DNA construct of claim 7; and
   (b) growing the transformed cell of step (a) under conditions suitable for the expression of the recombinant DNA construct.

10. A plant comprising the recombinant DNA construct of claim 7.

11. A seed comprising the recombinant DNA construct of claim 7.

12. A method for isolating a polypeptide having 1-deoxy-D-xylulose 5-phosphate synthase activity comprising isolating the polypeptide from a cell or culture medium of the cell, wherein the cell comprises a recombinant DNA construct comprising the polynucleotide of claim 1 operably linked to at least one regulatory sequence.

13. A method for evaluating at least one compound for its ability to inhibit 1-deoxy-D-xylulose 5-phosphate synthase activity, comprising the steps of:
   (a) introducing into a host cell the recombinant DNA construct of claim 7;
   (b) growing the host cell under conditions that are suitable for expression of the recombinant DNA construct wherein expression of the recombinant DNA construct results in production of a 1-deoxy-D-xylulose 5-phosphate synthase;
   (c) optionally purifying the 1-deoxy-D-xylulose 5-phosphate synthase from the host cell;
   (d) treating the 1-deoxy-D-xylulose 5-phosphate synthase with a compound to be tested;
   (e) comparing the activity of the 1-deoxy-D-xylulose 5-phosphate synthase that has been treated with a test compound to the activity of an untreated 1-deoxy-D-xylulose 5-phosphate synthase, and selecting compounds with potential for inhibitory activity.

* * * * *